United States Patent
Kunitomi et al.

(10) Patent No.: US 11,646,117 B2
(45) Date of Patent: May 9, 2023

(54) MATRIX FACTORIZATION OF ANTIBIOGRAM METADATA

(71) Applicant: International Business Machines Corporation, Armonk, NY (US)

(72) Inventors: Mark Kunitomi, San Francisco, CA (US); Dmitry Zubarev, San Jose, CA (US); Sarathkrishna Swaminathan, Santa Clara, CA (US)

(73) Assignee: International Business Machines Corporation, Armonk, NY (US)

( * ) Notice: Subject to any disclaimer, the term of this patent is extended or adjusted under 35 U.S.C. 154(b) by 769 days.

(21) Appl. No.: 16/430,856

(22) Filed: Jun. 4, 2019

(65) Prior Publication Data

US 2020/0388384 A1 Dec. 10, 2020

(51) Int. Cl.
*G16H 50/20* (2018.01)
*G16H 70/60* (2018.01)
(Continued)

(52) U.S. Cl.
CPC ............ *G16H 50/20* (2018.01); *G06F 17/16* (2013.01); *G16H 40/67* (2018.01); *G16H 70/40* (2018.01);
(Continued)

(58) Field of Classification Search
CPC ........ G16H 50/20; G16H 40/67; G16H 70/40; G16H 70/60; G16H 50/30; G06F 17/16;
(Continued)

(56) References Cited

U.S. PATENT DOCUMENTS

| 7,517,494 B2 | 4/2009 | Childers et al. |
| 9,659,145 B2 | 5/2017 | Sayood et al. |

(Continued)

FOREIGN PATENT DOCUMENTS

CN 110993113 A * 4/2020 ............ G16B 20/00

OTHER PUBLICATIONS

Yang et al., "Drug-Disease Association and Drug-Repositioning Predictions in Complex Diseases Using Causal Inference—Probabilistic Matrix Factorization", Aug. 13, 2014. (Year: 2014).*
(Continued)

*Primary Examiner* — Rachelle L Reichert
*Assistant Examiner* — Amanda R. Covington
(74) *Attorney, Agent, or Firm* — Cantor Colburn LLP; Daniel Johnson

(57) ABSTRACT

A method is described that utilizes non-negative matrix factorization to predict susceptibility of a microorganism to an antimicrobial drug. A sparse adjacency matrix is constructed from existing ground truth datasets that include antibiogram data and other data associated with microorganisms. The rows of the adjacency matrix correspond to biosamples, and the columns correspond to instances of metadata and drugs associated with one or more of the biosamples. The elements of the adjacency matrix are assigned non-zero numerical values or zero depending on whether a known association exists. The adjacency matrix is then factored using a selected number of latent factors, thereby producing a reconstruction matrix approximating the adjacency matrix. The values of the reconstruction matrix are used to predict antimicrobial susceptibility of a biosample ID to a drug when antibiogram data are lacking.

21 Claims, 15 Drawing Sheets

(51) Int. Cl.
G06F 17/16 (2006.01)
G16H 40/67 (2018.01)
G16H 70/40 (2018.01)
G06N 7/00 (2023.01)
G06N 20/00 (2019.01)

(52) U.S. Cl.
CPC ............... *G16H 70/60* (2018.01); *G06N 7/00* (2013.01); *G06N 20/00* (2019.01)

(58) Field of Classification Search
CPC .......... G06N 7/00; G06N 20/00; G16B 20/00; G16B 40/20; G16B 40/30
See application file for complete search history.

(56) References Cited

U.S. PATENT DOCUMENTS

| | | | |
|---|---|---|---|
| 9,677,109 B2 | 6/2017 | Shamsheyeva et al. | |
| 9,938,558 B2 | 4/2018 | Embree | |
| 2004/0219074 A1 | 11/2004 | Childers et al. | |
| 2013/0159221 A1* | 6/2013 | Thompson | G06F 11/3409 706/12 |
| 2014/0121985 A1 | 5/2014 | Sayood et al. | |
| 2014/0278136 A1 | 9/2014 | Shamsheyeva et al. | |
| 2017/0148085 A1* | 5/2017 | Tang | G06Q 30/0631 |
| 2017/0270244 A1 | 9/2017 | Murugesan et al. | |

OTHER PUBLICATIONS

Minnesota Department of Health, "About Antibiograms", Jan. 2015. (Year: 2015).*

Berry et al., "Algorithms and Applications for Approximate Non-negative Matrix Factorization," Computational Statistics & Data Analysis, vol. 52, Issue 1, Sep. 15, 2007, pp. 155-173.

Brbic et al., "Phenotype Inference from Text and Genomic Data," Conference Paper, Conference: ECML PKDD 2017, At Skopje, Macedonia, Jan. 2017.

Bro et al., "A fast non-negativity constrained linear least squares algorithm," Journal of Chemometrics, 1997, 11, 393-401.

Cai et al., "Learning Microbial Community Structures with Supervised and Unsupervised Non-negative Matrix Factorization," Microbiome (2017) 5:110.

Chu et al., "Optimality, computation, and interpretations of non-negative matrix factorizations," Jan. 2004, available at the internet address formed by the concatenation of "http://" and www.wfu.edu/plemmons".

Halko et al., "Finding structure with randomness: Probabilistic algorithms for constructing approximate matrix decompositions," SIAM Rev., 53(2):217-288 (May 2011).

Jiang et al., "Functional Biogeography of Ocean Microbes Revealed through Non-Negative Matrix Factorization," PLoS ONE, Sep. 2012 | vol. 7 | Issue 9 | e43866.

Koren et al., "Matrix Factorization Techniques for Recommender Systems," Computer, Published by the IEEE Computer Society, Aug. 2009, pp. 42-49.

Lee et al., "Algorithms for Non-Negative Matrix Factorization.," Advances in Neural Information Processing Systems, 2001, 13, 556-562.

McArthur et al., "The Comprehensive Antibiotic Resistance Database," Antimicrobial Agents and Chemotherapy p. 3348-3357, Jul. 2013, vol. 57, No. 7.

Muthu et al., "Studies on Antimicrobial Susceptibility Pattern of *Salmonella* Isolates From Chennai, India," International Journal of Pharma and Bio Sciences, 2011, vol. 2, issue 2, B-435-B-442.

Paatero et al., "Positive matrix factorization: A non-negative factor model with optimal utilization of error estimates of data values," Environmetrics, 1994, 5, 111-126.

Tandon et al., "Sparse nonnegative matrix approximation: new formulations and algorithms," Max Planck Institute for Biological Cybernetics, Technical Report No. 193, Sep. 13, 2010.

Yang et al., "Drug-Disease Association and Drug-Repositioning Predictions in Complex Diseases Using Causal Inference-Probabilistic Matrix Factorization," | J. Chem. Inf. Model. 2014, 54, 2562-2569.

Yang et al., "Microbial community pattern detection in human body habitats via ensemble clustering framework," BMC Systems Biology, 2014, 8(Suppl 4):S7.

Zhou et al., "Large-scale Parallel Collaborative Filtering for the Netflix Prize," AAIM, 337-348 (2008).

Muthu, "Studies on Antimicrobial Susceptibility Pattern of *Salmonella* Isolates From Chenn", International Journal of Pharma and Bio Sciences, vol. 2, Issue 2, 2011, 8p.

* cited by examiner

MATRIX FACTORIZATION OF ANTIBIOGRAM METADATA

BACKGROUND

The present invention relates to matrix factorization of antibiogram data, and more specifically, to predicting antibiotic resistance in the absence of ground truth data.

The surge of antibiotic resistance has made multidrug-resistant (MDR) bacterial infection a serious global threat. By 2050, an estimated ten million people will die each year from antimicrobial resistant (AMR) bacterial infection. Properly determining which antibiotics a particular microbe is resistant to and susceptible to can be the difference between life and death. Therefore, the problem of understanding the factors underlying bacterial antibiotic susceptibility and resistance is, and will continue to be, important to worldwide infection prognosis and treatment. The acceleration of the accumulation of data related to bacterial genomics and antibiotic resistance underscores the significance of the threat of antimicrobial resistance. As the rate of data accumulation increases, methods are needed for rapidly aggregating, cleaning, and analyzing the data. To this end, machine learning approaches to predicting AMR have the potential to scale with data and provide insights into this problem.

Antibiograms can be used to guide a clinician and/or pharmacist in the selection of the best antimicrobial treatment using empirical data from microbiology cultures and susceptibility results. Rapidly assessing the proper treatment for a bacterial infection can have drastic effects on the patient outcome. For example, patients with typhoid fever who go without timely and appropriate treatment are estimated to have a 30% mortality rate, whereas those receiving an early specific therapy have a mortality rate of 0.5%. A drawback of antibiograms is the need to culture an infecting microorganism, which can take days and delay results.

Previously produced antibiograms have potential use as a pool of data for detecting and analyzing trends in antimicrobial resistance as well as predicting features of current infections. When antimicrobial susceptibility testing data are summarized cumulatively for a hospital, healthcare system, or other health related network over time, trends in resistance can be identified and investigated.

However, the data can be sparse for datasets aggregated from many sources, especially those with a large number of potential measurements, because each source may have only collected data for a subset of features. This is particularly true of antibiotic resistance data (i.e., antibiograms) that are aggregated by the National Center for Biotechnology Information (NCBI).

Each source within the set of antibiograms has performed tests to examine the susceptibility/resistance of an isolate of bacteria to a number of different antibiotics. Since there are many antibiotics to test, no individual entry has tested their particular bacterial isolate against every antibiotic. The lack of observations for many antibiotics against many bacterial isolates limits the descriptive, and therefore, predictive power of machine learning approaches to classify these isolates. In addition, the predictions themselves may be an endpoint prediction whereby making a limited set of observations provides statistically supported predictions of features not empirically observed.

Methods are needed that draw from existing data originating from various sources, improve understanding of trends in antibiotic resistance, and enable predictions of antibiotic resistance in clinical or industrial settings for newly observed microbial isolates.

SUMMARY

Accordingly, a method is disclosed, comprising:

providing an initial matrix comprising rows corresponding to microorganisms and columns corresponding to metadata associated with one or more of the microorganisms, the metadata including antibiogram data, wherein an element of the initial matrix linking a microorganism to an antibiotic drug has a numerical value indicating no antibiogram data exist for the microorganism with respect to the antibiotic drug;

factoring the initial matrix using a matrix factorization algorithm, thereby forming a first factor matrix and a second factor matrix; and multiplying the first factor matrix by the second factor matrix, thereby forming a reconstruction matrix, wherein an element of the reconstruction matrix linking the microorganism to the antibiotic drug has a numerical value indicating the microorganism is resistant or susceptible to the antibiotic drug.

Also disclosed is a computer program product, comprising a computer readable hardware storage device having a computer-readable program code stored therein, said program code configured to be executed by a processor of a computer system to implement a method comprising:

providing an initial matrix comprising rows corresponding to microorganisms and columns corresponding to metadata associated with one or more of the microorganisms, the metadata including antibiogram data, wherein an element of the initial matrix linking a microorganism to an antibiotic drug has a numerical value indicating no antibiogram data exist for the microorganism with respect to the antibiotic drug;

factoring the initial matrix using a matrix factorization algorithm, thereby forming a first factor matrix and a second factor matrix; and multiplying the first factor matrix by the second factor matrix, thereby forming a reconstruction matrix, wherein an element of the reconstruction matrix linking the microorganism to the antibiotic drug has a numerical value indicating the microorganism is resistant or susceptible to the antibiotic drug.

Further disclosed is a system comprising one or more computer processor circuits configured and arranged to:

provide an initial matrix comprising rows corresponding to microorganisms and columns corresponding to metadata associated with one or more of the microorganisms, the metadata including antibiogram data, wherein an element of the initial matrix linking a microorganism to an antibiotic drug has a numerical value indicating no antibiogram data exist for the microorganism with respect to the antibiotic drug;

factor the initial matrix using a matrix factorization algorithm, thereby forming a first factor matrix and a second factor matrix; and multiply the first factor matrix by the second factor matrix, thereby forming a reconstruction matrix, wherein an element of the reconstruction matrix linking the microorganism to the antibiotic drug has a numerical value indicating the microorganism is resistant or susceptible to the antibiotic drug.

Also disclosed is a method, comprising:

acquiring antibiogram data that include a table in which the rows correspond to biological samples and the columns correspond to categories of metadata;

transforming the table to an adjacency matrix;

analyzing the adjacency matrix with a matrix factorization algorithm, thereby finding two factor matrices, and then computing a reconstructed adjacency matrix that is the product of the two factor matrices; and comparing the adjacency matrix to the reconstructed adjacency matrix in an entry-wise fashion.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

FIG. 7B shows the number of test samples per antibiotic. FIG. 7A shows the error rate above each antibiotic.

DETAILED DESCRIPTION

Figure 1:
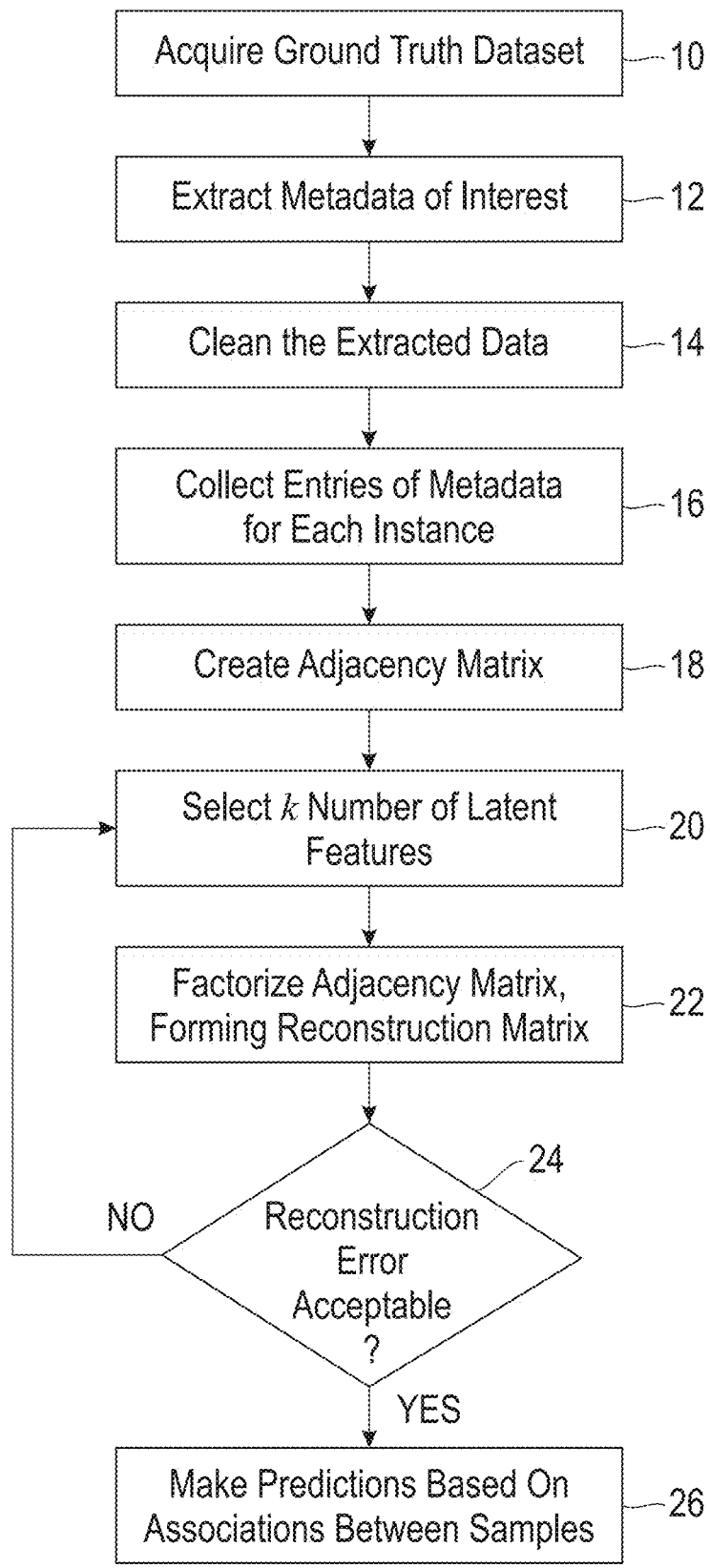
FIG. 1 is a flow diagram showing a preferred embodiment of the disclosed method.

A method is described for predicting antibiotic resistance and susceptibility of microorganisms from genomic data and metadata of the microorganisms before antibiogram testing takes place. The method recasts existing knowledge of a microorganism's genomic data and metadata, which is contained in existing databases, in the form of an association matrix (adjacency matrix, initial matrix) between the genomic data and the metadata. The method carries out a latent factor analysis on the association matrix using matrix factorization, reconstructs the association matrix from the results of the latent factor analysis, and predicts new associations from the reconstructed association matrix (reconstructed matrix). With sufficient initial genomic data and metadata, the new associations can allow predictions of antibiotic resistance and/or susceptibility of a microorganism to one or more medical therapies before direct testing takes place. The matrix factorization can be applied to the metadata prediction in a purely data-centric manner without evaluating the similarity between instances of genomic data and metadata. The disclosed method is adaptable to machine learning.

Matrix factorization (MF) is a form of latent factor analysis broadly applied in recommender systems. It enables prediction of associations between objects, such as shoppers and products, viewers and movies, etc., via linear decomposition of the full-rank observation matrix into low-rank components. As a form of latent factor analysis, MF has been used for clustering tasks in microbiology. Reported applications of MF in this domain include detection of microbial communities in complex environments at the level of organism and ocean habitats, dimensionality reduction in microbiome data, and phenotype assignment.

The disclosed method utilizes MF to analyze existing biosample data that include measured drug interactions of a first set of microorganisms to predict drug interactions of a second set of microorganisms for which drug interaction data does not exist. This is accomplished by analyzing other non-drug related metadata of the biosample data to discover associations linking microorganisms of the first and second sets.

Definitions

An "adjacency matrix" is a sparse matrix produced from one or more ground truth datasets in which the rows correspond to biosample IDs (microorganisms) and columns correspond to instances of metadata, including antibiotic drugs, associated with one or more of the biosample IDs. The elements of the matrix are assigned non-zero numerical values or zero depending on whether an association exists or not. The values can be assigned manually or programmatically.

An "antibiogram" is a profile of antimicrobial susceptibility of a microorganism to one or more antimicrobial drugs.

An "antimicrobial" is a drug that kills microorganisms or inhibits their growth.

"Antimicrobial resistance is the ability of a microorganism to continue to grow/live in the presence of an antimicrobial material.

Herein, a "database" is an electronic file for storing and retrieving data. Databases are also referred to herein as data tables. Data tables comprise rows and columns (i.e., fields) of data. The rows are formally called tuples or records. A data table comprises one or more records, each record comprising one or more defined fields having respective defined data types (e.g., text, numeric, date, time, memo, and so on) and defined field lengths where applicable. A working data table comprises at least one record containing data in one or more fields of the record. The data tables are located on data storage devices, which can be remote or local relative to the user input/output devices. A "database system" comprises at least one data table and a database management software program for managing the storage and retrieval of data to and from the data tables. The database management programs can be remote or local relative to the data tables and/or the end user. A Relational Database Management System (RDBMS) is a database management system (DBMS) that uses relational techniques for storing and retrieving data using data tables. A relational database system can have many data tables, and each data table can have multiple records and multiple fields within each record. A data table in a relational database system can be accessed using an index. An index is an ordered set of references (e.g., pointers) to the records or rows in a data table. The index is used to access each record in the file using a key (e.g., one or more of the fields of the record or attributes of the row). Without an index, finding information in a large data table would require a resource-intensive time-consuming scan (e.g., linearly) of each record of a table. Indexes provide a faster alternate technique of accessing data contained in one or more data tables that are linked by a common key. Users can create indexes for a table after the table is built. An index is based on one or more columns (fields) of a given table.

"DNA" is deoxyribonucleic acid.

A "false positive" is an output that incorrectly indicates that a particular condition or attribute is present.

A "gene" is the basic unit of heredity, a linear sequence of nucleotides along a segment of DNA that provides the coded instructions for synthesis of RNA, which, when translated into protein, leads to the expression of a hereditary trait.

A "genome" is the total genetic content of a microorganism. In the case of bacteria, the genome is DNA.

"Genome assembly" refers to a process of aligning and merging a set of sequence fragments that were derived from a larger genome in order to reconstruct the original sequence.

A "ground truth dataset" is a dataset formed by direct observation (measured data) as opposed to data obtained by inference or assumption. A ground truth dataset is fact-based data that has been observed or measured, and can be analyzed objectively.

"High-throughput sequencing" (HTS) is any method of sequencing a nucleic acid that is highly parallel. A genome or metagenome is cut into a large number of fragments, and the fragments are sequenced in parallel.

"Latent factors" of a given biosample ID are the elements of the row of factor matrix B associated with the given biosample ID. The latent factors of a given drug (antibiotic) are the elements of the column of factor matrix A associated with the given drug. Factor matrices B and A are produced by factorization of the adjacency matrix.

A "matrix" is a rectangular array of elements (cells), the elements having quantitative values or expressions (entry values, or simply entries). A matrix has at least one row and at least one column of elements. An m×n matrix has m rows and n columns, where m and n are independent positive integers. Numerical entry values can be positive numbers, negative numbers, or zero.

A "protein" is a polymer composed of amino acids joined together by peptide bonds.

A "microbiome" is a community of microorganisms that inhabit a particular environment (e.g., microbes of the human gut), or a sample taken therefrom.

"RNA" is ribonucleic acid.

Herein, a "sparse matrix" means a matrix or array in which many or most of the elements are zero. An element having a zero value can indicates a negative response by the microorganism or the response is unknown. For example, a zero value with respect to resistance phenotype of a microorganism to a drug can indicate the microorganism is susceptible to the drug, or the microorganism has not been tested against the drug unknown).

"Taxonomy" is a biological scheme of classification of organisms. Herein, for bacteria, the hierarchy is domain, kingdom, division, phylum, class, order, family, genus, species, sub-species, serovar, and strain. Each of the foregoing classifications is a "rank" on the taxonomic tree.

A "taxonomic tree" herein is a data structure for classifying organisms. The taxonomic tree comprises nodes (i.e., taxa, singular taxon) that are grouped into "parent nodes" linked to "child nodes". Parent nodes are depicted above child nodes in a tree diagram. Child nodes are taxonomic descendants of parent nodes. For example, a genus (parent node) can be linked to two or more species (child nodes). The taxonomic tree can be rooted (i.e., known ancestral root) or unrooted (i.e., unknown ancestral root), bifurcating (i.e., two child nodes per parent node) or multi-furcating (i.e., more than two child nodes per parent node). Typically, the taxonomic tree is in the form of a "binary tree" (i.e., each parent node has two child nodes). A "leaf node" is a child node having no descendants (e.g., the species of a genus). In the self-consistent taxonomy, each leaf node has one genome. "Internal nodes" are all nodes other than the leaf nodes.

Method

FIG. 1 is a flow diagram showing the steps of implementing the disclosed method. The process begins by acquiring a ground truth dataset 10 that contains observations and/or measurements made on one or more biosamples. The ground truth data can be pulled from a single source or multiple source(s) (e.g., NCBI, hospital laboratories). The data should be in the form of a biosample identification (ID) and observations associated with each biosample ID. A biosample ID is an accession number for a given microorganism. The ground truth data can contain, for example, the source of the given microorganism, taxonomic information of the given microorganism, nucleic acid sequencing data of the given microorganism, antibiogram data obtained for the given microorganism, and other pertinent information. Each given sample ID can have many associated observations.

The metadata of interest are extracted from the ground truth dataset 12 and then cleaned 14, which means transforming the extracted data into either discrete or continuous values depending on the method of matrix factorization used. For example, the ground truth metadata can contain a category "Isolation source", where an instance of this category can be "wound", "blood", "sputum", "urine", etc. Each of these instances of isolation source can be assigned a one or a zero for a given biosample ID, where a one indicates the biosample was isolated from the source and a zero indicates it was not. As another example, the ground truth metadata can contain a category for the drug "amoxicillin", where instances of this category for a given biosample ID can be "susceptible," "susceptible-dose-dependent," "intermediate," "non-susceptible," and "resistant." In this case, instances "susceptible," "susceptible-dose-dependent," "intermediate," can be assigned a value of 0, meaning susceptible, and instances "non-susceptible," and "resistant" can be assigned a value of 1, meaning resistant.

The metadata entries are then collected 16, and an adjacency matrix R (initial matrix) is created 18. The adjacency matrix R is an m×n matrix containing m rows of biosample IDs and n columns of metadata instances and/or categories, with entries being the assigned values. For example, one column of the adjacency matrix can be "wound", another column "blood", another column "sputum", another column "amoxicillin", with corresponding entries of 1 or 0 for a given biosample ID. The adjacency matrix R is the matrix to be factored.

The choice of k is determined by an iterative process comprising i) choosing an initial number of latent features k', 20 ii) factorizing the adjacency matrix into an m×k' first factor matrix B and a k'×n second factor matrix A, where the product of A×B is Q, and Q is a reconstruction matrix that approximates R, 22 and iii) determining whether the reconstruction error is acceptable, 24. The reconstruction error is based on the differences between Q and R, which can be measured as the Frobenius norm. If the reconstruction error is not acceptable, a new value of k' is selected and the process repeated until the reconstruction error is acceptable, at which point k'=k. The reconstruction matrix formed by the matrix factorization using k latent factors is then inspected for differences with adjacency matrix R. The non-zero differences reveal latent associations between biosamples of the reconstruction matrix Q, which can then used to make predictions based on the associations. An association is recognized when the reconstruction matrix Q contains a non-zero element and the corresponding element in R is zero.

Matrix Factorization Algorithms

Algorithms for matrix factorization (decomposition) with estimated performance bounds and efficient scalable implementations are available. The following are exemplary: LU decomposition, LU reduction, Block LU decomposition, Rank factorization, Cholesky decomposition, QR decomposition, RRQR factorization, Interpolative decomposition, Eigendecomposition, Jordan decomposition, Schur decomposition, Real Schur decomposition, QZ decomposition, Takagi's factorization, Singular value decomposition, Scale-invariant decompositions, Polar decomposition, Algebraic polar decomposition, Mostow's decomposition, Sinkhorn normal form, Sectoral decomposition, and Williamson's normal form.

More specific non-negative algorithms for matrix factorization include the multiplicative update algorithm of Lee, D. and Seung, H., "Algorithms for Non-Negative Matrix Factorization.," Advances in Neural Information Processing Systems, 2001, 13, 556-562; the gradient descent algorithm of Chu, M., Diele, F., Plemmons, R., Ragni, S., "Optimality, computation, and interpretations of nonnegative matrix factorizations," January 2004, available at the internet address formed by the concatenation of "http://" and "www.wfu.edu/~plemmons"; the alternating least squares algorithm of Paatero, P., Tapper, U., "Positive matrix factorization: A non-negative factor model with optimal utilization of error estimates of data values,"; and the fast non-negative least squares algorithm of Bro, R., de Jong, S., "A fast non-negativity constrained linear least squares algorithm," Journal of Chemometrics, 1997, 11, 393-401.

The following references provide additional details: Berry, M. W., Browne, M., Langville, Amy N., Pauca, V. P., and Plemmons, R. J., "Algorithms and Applications for Approximate Nonnegative Matrix Factorization," Computational Statistics and Data Analysis, 2007, Volume 52, Issue 1, Pages 155-173; and N. Halko, P. G. Martinsson, and J. A. Tropp, "Finding structure with randomness: Probabilistic algorithms for constructing approximate matrix decompositions," SIAM Rev., 53(2):217-288 (May 2011). Alternative-least-squares with weighted-k-regularization (ALS-WR) has been used to calculate a feature matrix using an item interaction matrix and an item feature matrix (Y. Zhou, D. Wilkinson, R. Schreiber, and R. Pan, "Large-scale Parallel Collaborative Filtering for the Netflix Prize," AAIM, 337-348 (2008)).

The preferred algorithm is non-negative matrix factorization initialized by singular value decomposition (SVD), suitable for a square or non-square matrix (i.e., m×n matrix).

Implementation of the Method

The following example illustrates the practice of the invention. Matrix factorization was used to predict resistance of microorganisms to drugs from genomic data and associated metadata obtained from a public source (NCBI).

A ground truth dataset was acquired from NCBI's biosample database using a query for organisms classified as bacteria and filtered for records with associated antibiogram metadata. Data for the resulting accessions were downloaded from NCBI and reformatted into a suitable format (tab separated values with headers). In order to cross-validate predictions made using the disclosed method, a subset of the available data, designated initial dataset, was used for the matrix factorization.

The initial dataset is a data table where rows are samples of microorganisms identified by their biosample IDs and columns are "metadata categories" ("attributes" at NCBI). Metadata categories of a given biosample ID include organism, family name, family taxonomic identification (TaxID), breed, cell line, cell type, collection date, collected by, cultivar, disease, geographic location, latitude and longitude, host disease, isolation source, sex, strain, tissue, type. The entries in the table are "instances" of metadata categories associated with a given biosample ID. As an example, the organism and taxonomy of SAMN07265011 is the species (instance *Klebsiella pneumoniae*), genus (instance *Klebsiella*), family (instance Enterobacteriaceae), order (instance Enterobacterales), class (instance Gammaproteobacteria), phylum (instance Proteobacteria), and super kingdom (instance Bacteria). An instance of metadata category "Isolation Source" for biosample ID SAMN07265011 is "wound", as shown in Table 1. Another instance of metadata category "Isolation Source" is "urine" for a biosample IDs SAMN02356583 and SAMN02581401.

TABLE 1

| Biosample ID | Strain | Collected By | Collection Date | Geographic Location | Host | Host Disease | Isolation Source | Latitude And Longitude | Type |
|---|---|---|---|---|---|---|---|---|---|
| SAMN07265011 | DHQP1605752_NV | Washoe County Health District | Aug. 19, 2016 | USA: Nevada | *Homo sapiens* | | wound | | MLST-15 |
| SAMN02356583 | BDMC 44 | | Jan-13 | USA: Boston, MA | *Homo sapiens* | | urine | | |
| SAMN02581401 | BDMC 82 | | Nov-2013 | outpatient | *Homo sapiens* | | urine | | |

An antibiogram has rows for each antibiotic tested against a given microorganism and a column for resistance phenotype (a qualitative rating for the level of resistance observed). Table 2 shows an example of antibiogram data for biosample ID SAMN07265011 obtained from NCBI.

TABLE 2

| Antibiotic | Resistance phenotype | Measurement sign | Measurement | Measurement units | Laboratory typing method | Laboratory typing platform | Vendor | Laboratory typing method version or reagent | Testing standard |
|---|---|---|---|---|---|---|---|---|---|
| amikacin | resistant | > | 64 | mg/L | MIC | | | | CLSI |
| ampicillin | resistant | > | 32 | mg/L | MIC | | | | CLSI |
| aztreonam | resistant | > | 64 | mg/L | MIC | | | | CLSI |
| cefazolin | resistant | > | 8 | mg/L | MIC | | | | CLSI |
| cefepime | resistant | > | 32 | mg/L | MIC | | | | CLSI |
| cefotaxime | resistant | > | 64 | mg/L | MIC | | | | CLSI |
| cefotaxime-clavulanic acid | not defined | > | 32/4 | mg/L | MIC | | | | CLSI |
| cefoxitin | resistant | > | 16 | mg/L | MIC | | | | CLSI |
| ceftazidime | resistant | > | 128 | mg/L | MIC | | | | CLSI |
| ceftazidime-clavulanic acid | not defined | > | 64/4 | mg/L | MIC | | | | CLSI |
| ceftriaxone | resistant | > | 32 | mg/L | MIC | | | | CLSI |
| chloramphenicol | resistant | > | 16 | mg/L | MIC | | | | CLSI |
| ciprofloxacin | resistant | > | 8 | mg/L | MIC | | | | CLSI |
| colistin | not defined | > | 8 | mg/L | MIC | | | | CLSI |
| doripenem | resistant | > | 8 | mg/L | MIC | | | | CLSI |
| ertapenem | resistant | > | 8 | mg/L | MIC | | | | CLSI |
| fosfomycin | not defined | == | 16 | mg/L | MIC | | | Etest | CLSI |
| fosfomycin | not defined | == | 32 | mg/L | MIC | | | Agar dilution | CLSI |
| gentamicin | resistant | > | 16 | mg/L | MIC | | | | CLSI |
| imipenem | resistant | == | 32 | mg/L | MIC | | | | CLSI |
| levofloxacin | resistant | > | 8 | mg/L | MIC | | | | CLSI |
| meropenem | resistant | > | 8 | mg/L | MIC | | | | CLSI |
| piperacillin-tazobactam | resistant | > | 128/4 | mg/L | MIC | | | | CLSI |
| polymyxin B | not defined | > | 8 | mg/L | MIC | | | | CLSI |
| tetracycline | resistant | > | 32 | mg/L | MIC | | | | CLSI |
| tigecycline | intermediate | == | 4 | mg/L | MIC | | | | CLSI |
| tobramycin | resistant | > | 16 | mg/L | MIC | | | | CLSI |
| trimethoprim-sulfamethoxazole | resistant | == | 8/152 | mg/L | MIC | | | | CLSI |
| ceftazidime-avibactam | resistant | == | 16/4 | mg/L | MIC | | | | CLS |

The next step is to transform the biosample metadata and associated antibiogram metadata into an adjacency matrix suitable for analysis via matrix factorization. Entries from the initial dataset are collected and unique instances of metadata are identified from the entries. The adjacency matrix is a table formed where rows are unique samples identified by their biosample IDs, the columns are unique "instances" of metadata (e.g., wound, urine, homosapiens) or category of metadata (e.g., specific drug) and the entries are is (ones) for the pairs of biosample IDs and metadata instances that have been observed, and Os (zeros) otherwise. The example entries of Table 1 are represented in the adjacency matrix as shown below in Table 3. Table 3 is a portion of the adjacency matrix transformation of the initial data of Table 1 and Table 2. For example, the entry for the row "SAMN07265011", column "homosapiens" is 1, column "wound" is 1, column "urine" is 0, and column "cefoxitin" is 1.

TABLE 3

| Biosample ID | Homosapiens | Wound | Urine | Cefoxitin |
|---|---|---|---|---|
| SAMN07265011 | 1 | 1 | 0 | 1 |
| SAMN02356583 | 1 | 0 | 1 | 0 |
| SAMN02581401 | 1 | 0 | 1 | 0 |

The adjacency matrix, designated R, is an m×n matrix, where m represents the number of rows of biosample IDs and n represents the number of columns corresponding to unique instances of metadata. Contained in the unique instances of metadata are antibiogram testing results, if available, for a given biosample ID. Each biosample ID can be tested against zero or more antibiotics. Biosamples can be, and generally are, tested against different antibiotics, making the adjacency matrix sparsely filled. Each antibiotic of the antibiogram becomes an instance of metadata (therefore a column header) in the adjacency matrix as shown for cefoxitin in Table 3. The antibiotics whose "resistance phenotype" is "resistant" or "intermediate" for SAMN07265011 are given a "1" in the adjacency matrix because "resistant" and "intermediate" are interpreted as being positively resistant to the drug. Those whose "resistance phenotype" is "not defined" or "unknown" are given a "0" in the adjacency matrix. For example, entries for biosamples SAMN02356583 and SAMN02581401 under the drug cefoxitin in Table 3 are unknown (have not been reported at this time) and therefore are assigned a zero.

The adjacency matrix R, which is a sparse matrix having many empty cells, can now be analyzed using matrix factorization. The object of the matrix factorization is to factor adjacency matrix R into two non-negative matrices, designated B (for biosamples) and A (for antibiotics), such that the product of B×A=Q approximates R. R is the input matrix to the factorization, B and A are the resulting factor matrices, and Q is a reconstruction matrix approximating R. In this instance, each value of each entry of factor matrices B and A is either 0 or a positive number.

To conserve computer resources, the adjacency matrix R was limited to 500 biosample IDs and 547 unique metadata instances. Factor matrix B is therefore a 500 (biosample IDs)×k dimensional matrix and factor matrix A is a k×547 (metadata including antibiotics) dimensional matrix, where k is the number of latent factors used in the factorization (see further below for discussion of latent factors). The upper limit of k depends on the size of matrix R, and therefore also on the sizes of factor matrices B and A. The value of k is generally less than the minimum of the set of number of rows of B and number of columns of A (i.e., if R is an m×n matrix, B has m rows and A has n columns, then k<min(m, n)). Typically, k is chosen such that k<<min(m, n). With this restriction in mind, k can be a positive integer greater than 0, more specifically between 0 and 1,000,000, even more specifically between 0 and 1000, and still more specifically between 0 and 100.

R is a subset of a field $\mathbb{R}$ having dimensions of all biosample IDs×all metadata instances, B is a subset of the field $\mathbb{B}$ having dimensions of all biosample IDs×all latent factors, and A is a subset of the field $\mathbb{A}$ having dimensions of all latent factors×all metadata instances.

$$B \times A = Q \sim R$$

$B \in \mathbb{B}$ Biosample IDs×Latent factors $A \in \mathbb{A}$ Latent factors×Metadata instances The factorization process begins by selecting a value of k (i.e., the number of latent factors), populating B and A with non-negative random values, and iteratively changing k while monitoring the convergence of Q to R. The difference between Q and R is the reconstruction error. The entries of B and A remain positive throughout the iterations. The ultimate choice of k can be influenced not only by considerations of minimizing the reconstruction error but also on conserving computation time for a given computer hardware configuration (i.e., based on the amount of available computer memory, processing speed, and so on).

In the present example, the reconstruction error was calculated as the Frobenius norm of the residual matrix Z, where Z=R−AB=R−Q. The elements of Z are measures of the difference between the corresponding entries of the original adjacency matrix R and the reconstructed matrix Q. The reconstruction error can be minimized by minimizing the Frobenius norm of Z. Z is an m×n matrix (just as are R and Q). The Frobenius norm of Z, expressed as $\|Z\|_F$, is the square root of the sum of the absolute squares of its entries, $z_{ij}$:

$$\|Z\|_F = \sqrt{\sum_{i=1}^{m} \sum_{j=1}^{n} |z_{i,j}|^2}$$

Figure 2:
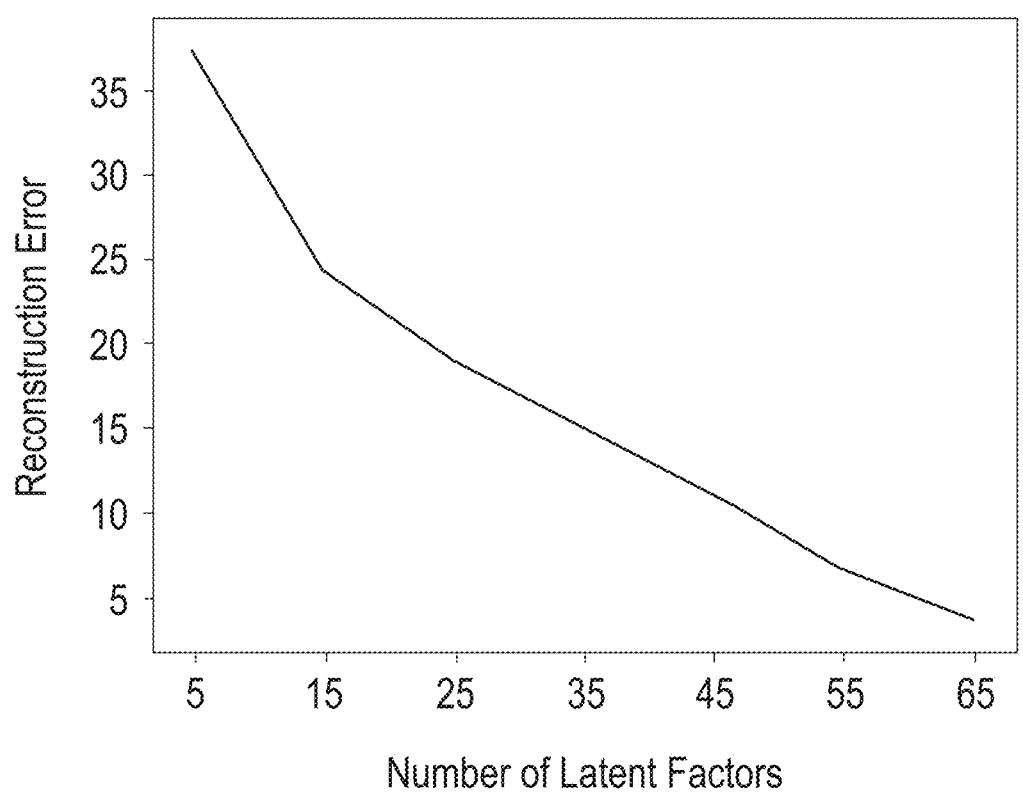
FIG. 2 is a graph showing the reconstruction error as a function of number of latent factors k in the factorization of the adjacency matrix.

FIG. 2 (graph) shows the reconstruction error (i.e., error between Q and original matrix R) as a function of the number of latent factors k. The plot in FIG. 2 shows a monotonic decrease of the reconstruction error with increasing number of latent factors, but the rate of the error change remains roughly constant beyond 15 latent factors. Therefore, 15 latent factors were selected to make predictions about associations between the biosample IDs and the metadata. In this manner, the dependence of the reconstruction error on the number of latent factors was used to determine a lower bound of k for predicting antibiotic resistance, thereby conserving computer resources.

Latent Factors

Non-negative matrix factorization effectively performs dimensionality reduction of the initial data. Dimensions in this reduced dimensionality representation are called "latent factors". Therefore, latent factors are variables that are not directly observed but are rather inferred (through non-negative matrix factorization) from other variables that are observed. Latent factors do not have pre-defined interpretations; they come from the data.

Returning to the method, matrix factorization predicts that there is an association between a row and a column of the adjacency matrix R if the respective entry in the adjacency matrix R is 0 and the same entry in reconstruction matrix Q is a non-zero number. Predicted associations can have different interpretations depending on the metadata used. The predicted resistance value q of a given biosample ID, b, to a given antibiotic a, of matrix Q can be computed as follows:

$$q_{ba} = \sum_{k=1}^{k \; latent \; factors} B_{b,k} A_{k,a}$$

Utility

The utility of the disclosed methods is further illustrated by the following hypothetical examples.

In the first example, biosample "SAMN02356583" is associated with metadata instances "Yersiniaceae" and "1903411" (metadata categories "Family name" and "Family TaxID", respectively) in the adjacency matrix. Matrix factorization could predict an association of this biosample with metadata instance "543", which belongs to the category "Family TaxID" of Enterobacteriaceae. The interpretation of this hypothetical predicted association is that the metadata of the biosample in question shows the same patterns as the metadata of samples associated with Family TaxID of Enterobacteriaceae.

In another hypothetical example, biosample "SAMN02581401" is associated with metadata instance "urine" (metadata category "Isolation Source") in the adjacency matrix. Matrix factorization may predict an association of this biosample with metadata instance "blood", suggesting that the pattern of the metadata associated with this biosample is similar to the biosamples isolated from blood.

For each of these hypothetical examples the derived association between different observations can be inherently useful in describing similarities that may be unanticipated such as a similarity between isolates found in blood and urine. The derived associations can also be useful in predicting unknown entries. This is of particular importance when some instances of the sample can quickly and easily be determined such as the isolation source or the family or genus of the bacteria, whereas other instances such as antimicrobial resistance may take days to determine.

In another hypothetical example, there can be 5 metadata instances in "Resistance Phenotype" category: "susceptible," "susceptible-dose-dependent," "intermediate," "non-susceptible," and "resistant." During the transformation from the metadata table to the adjacency matrix, the latter three instances may be interpreted as presence of resistance. In this instance, the entries in the adjacency matrix for the respective biosample and antibiotic can be set to 1 (or a first non-negative number). Other metadata instances may be interpreted as the absence of resistance, for which the entries in the adjacency matrix for the respective biosample and antibiotic can be set to 0 (or a second non-negative number). If the information about resistance phenotype with respect to a specific antibiotic is not available, the entry of the adjacency matrix can also be set to 0, the second non-negative number, or a third non-negative number).

To test the factorization process, the adjacency dataset can be set up to exclude known information about the Resistance Phenotype of a biosample ID to a particular drug (e.g., "SAMN02646214" with respect to the antibiotic "ceftriaxone"). For example, the element corresponding to SAMN02646214/ceftriaxone (row/column) of the adjacency matrix can be set to 0. Matrix factorization may then result in a respective element of the reconstruction matrix having a value of 1, which means that the biosample in question is expected to be resistant to this antibiotic. Inspection of the data withheld during the construction of the example dataset shows that "Resistance Phenotype" of biosample ID "SAMN02646214" with respect to antibiotic "ceftriaxone" is "intermediate". This would be a confirmation of the prediction of matrix factorization.

In a similar manner, the example dataset could withhold information about the "Resistance Phenotype" of biosample SAMN02646214 with respect to the antibiotic ampicillin. Matrix factorization could predict that biosample SAMN02646214 should be resistant to antibiotic "ampicillin", in agreement with the withheld data.

Actual examples of matrix factorization are described further below.

Samples

Herein, a biosample, or simply "sample", contains at least one microorganism and/or the sequenced nucleic acid of at least one microorganism. The ground truth dataset includes an accession identification given to the sample, taxonomic identification of at least one microorganism of the sample, sequence data of the microorganism(s), and any metadata associated with the sample and/or microorganism(s). Samples include water samples obtained from tap water, lakes, streams, field runoff, and sewage; swabbed samples from contact surfaces (e.g., building surfaces, countertops, furniture, utensils, clinical instruments, computer hardware, cell phones, door handles, doors, windows, screens, cabinets, cabinet doors, sinks, faucet); animal samples (e.g., blood, blood plasma, serum, cells, a cellular extract, a cellular aspirate, expectorant, sputum, saliva, mucous, urine, sweat, tears, swabs from wounds); and samples obtained from food, food-handling equipment, and surfaces contacted by food. The samples can be a solid or liquid, containing water or no water.

Other samples comprise at least one microorganism submitted to antibiogram testing. An antibiogram comprises a rating of susceptibility or resistance of a given microorganism to one or more drugs. These samples also include metadata (e.g., isolation source, date of testing, source of drug, etc.).

Microorganisms

Microorganisms include bacteria, fungi, viruses, protozoans, and parasites.

Exemplary non-limiting bacterial species include *Acetobacter aurantius, Acinetobacter baumannii, Actinomyces israelii, Agrobacterium radiob acter, Agrobacterium tumefaciens, Anaplasma phagocytophilum, Azorhizobium caulinodans, Azotobacter vinelandii, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacillus Thuringiensis, Bacteroides fragilis, Bacteroides gingivalis, Bacteroides melaninogenicus* (also known as *Prevotella melaninogenica*), *Bartonella henselae, Bartonella quintana, Bordetella, Bordetella bronchiseptica, Bordetella pertussis, Borrelia afzelii, Borrelia burgdorferi, Borrelia garinii, Borrelia recurrentis, Brucella abortus, Brucella canis, Brucella melitensis, Brucella suis, Burkholderia mallei, Burkholderia pseudomallei, Burkholderia cepacia, Calymmatobacterium granulomatis, Campylobacter, Campylobacter coli, Campylobacter fetus, Campylobacter jejuni, Campylobacter pylori, Chlamydophila pneumoniae* (previously called *Chlamydia pneumoniae*), *Chlamydophila psittaci* (previously called *Chlamydia psittaci*), *Chlamydia trachomatis, Clostridium botulinum, Clostridium difficile, Clostridium perfringens* (previously called *Clostridium* welchii), *Clostridium tetani, Corynebacterium diphtheriae, Corynebacterium fusiforme, Coxiella burnetii, Ehrlichia canis, Ehrlichia chaffeensis, Enterobacter cloacae, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus bulgaricus, Lactobacillus casei, Lactococcus lactis, Legionella pneumophila, Leptospira interrogans, Leptospira santarosai, Leptospira weilii, Leptospira noguchii, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycob acterium lepraemurium, Mycobacterium phlei, Mycob acterium smegmatis, Mycobacterium tuberculosis, Mycobacterium ulcerans, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Prevotella melaninogenica* (previously called *Bacteroides melaninogenicus*), *Pseudomonas aeruginosa, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Shigella sonnei, Spirillum volutans, Streptococcus agalactiae, Staphylococcus aureus, Staphylococcus epidermidis, Staphylococcus saprophyticus, Stenotrophomonas maltophilia, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Streptococcus viridans, Treponema pallidum, Treponema denticola, Ureaplasma urealyticum, Vibrio cholerae, Vibrio comma, Vibrio parahaemolyticus, Vibrio vulnificus, Yersinia enterocolitica, Yersinia pestis, Yersinia pseudotuberculosis,*

Non-limiting exemplary viruses include Adenovirus, Herpes simplex, type 1, Herpes simplex, type 2, Varicella-zoster virus, Epstein-barr virus, Human cytomegalovirus, Human herpesvirus, type 8, Human papillomavirus, BK virus, JC virus, Smallpox, Hepatitis B virus, Parvovirus B19, Human astrovirus, Norwalk virus, coxsackievirus, hepatitis A virus, poliovirus, rhinovirus, Hepatitis C virus, yellow fever virus, dengue virus, West Nile virus, TBE virus, Rubella virus, Hepatitis E virus, Human immunodeficiency virus (HIV), Influenza virus, Lassa virus, Crimean-Congo hemorrhagic fever virus, Hantaan virus, Ebola virus, Marburg virus, Measles virus, Mumps virus, Parainfluenza virus, Respiratory syncytial virus, Rabies virus, Rotavirus, Orbivirus, Coltivirus, Banna virus, and zika virus.

Non-limiting exemplary fungi include *Candida albicans, Aspergillus fumigatus, Aspergillus flavus, Aspergillus clavatus, Cryptococcus neoformans, Cryptococcus laurentii, Cryptococcus albidus, Cryptococcus gattii, Histoplasma capsulatum, Pneumocystis jirovecii, Pneumocystis carinii,* and *Stachybotrys chartarurn.*

Non-limiting exemplary protozoa include *Entamoeba histolytica, Entamoeba coli, Entamoeba dispar, Entamoeba moshkovskii, Entamoeba* Bangladeshi, *Entamoeba hartmanni, Dientamoeba fragilis, Endolimax nana,* lodarnoeba *butschlii, Plasmodium malariae, Plasmodium falciparum, Plasmodium vivax, Plasmodium ovale, Naegleria fowleri, Acanthamoeba species, Balamuthia mandrillaris, Sappinia diploidea, Giardia larnblia, Giardia intestinalis, Giardia duodenalis, Toxoplasma gondii, Nippostrongylus brasiliensis, Cryptosporidium parvum, Cryptosporidium hominis, Cryptosporidium cams, Cryptosporidium felis, Cryptosporidium meleagridis, Cryptosporidium muris, Trichomonas vaginalis, Trypanosoma cruzi, Leishmania major, Leishmania tropica, Leishmania barziliensis, Leishmania mexicana, Leishmania guyanesis, Leishmania panamensis*, and *Trypanosoma brucei.*

Antibiotics

Non-limiting antibiotics include (listed by common name): G418, GE2270A, GE37468, Imipenem-EDTA-PA, L-681,217, SB22484, UK-69,753, acridine dye, acriflavin, actinomycin, actinomycin D, amikacin, amoxicillin, amoxicillin-clavulanic acid, amoxicillin-clavulanic acid, ampicillin, ampicillin-sulbactam, amythiamicin A, antibiotic A40926, antibiotic A47934, apramycin, arbekacin, arsphenamine, arylomycin, astromicin, aurodox, avoparcin, azamulin, azdimycin, azidamfenicol, azithromycin, azlocillin, aztreonam, bacitracin, bacitracin A, bacitracin B, bacitracin F, balhimycin, benzylpenicillin, bicyclomycin, bleomycin, bleomycin A2, bleomycin B2, bleomycinic acid, brodimoprim, butirosin, capreomycin, carbenicillin, carbomycin, cefaclor, cefadroxil, cefalexin, cefalotin, cefamandole, cefazolin, cefdinir, cefditoren, cefepime, cefetamet, cefixime, cefmetazole, cefonicid, cefoperazone, cefotaxime, cefotaxime-clavulanic acid, cefotetan, cefotiam, cefoxitin, cefpodoxime, cefpodoxime-proxetil, cefprozil, ceftaroline, ceftazidime, ceftazidime-avibactam, ceftazidime-clavulanic acid, ceftibuten, ceftiofur, ceftizoxime, ceftobiprole, ceftolozane-tazobactam, ceftriaxone, cefuroxime, celesticetin, cephalexin, cephalothin, cephamycin, cephapirin, cephem, cephradine, chalcomycin, chloramphenicol, chloroeremomycin, chlortetracycline, cinoxacin, ciprofloxacin, clarithromycin, clavulanic acid, clinafloxacin, clindamycin, clofazimine, clorobiocin, cloxacillin, colistin, colistin A, colistin B, coumermycin A1, cyclic thiazolyl peptide elfamycin, cycloserine, dalbavancin, dalfopristin, danofloxacin, daptomycin, defensin, demeclocycline, diaminopyrimidine, dibekacin, dicloxacillin, dihydromocimycin, dirithromycin, doripenem, doxycycline, edeine, edeine A, edeine B, edeine D, edeine F, efrotomycin, elfamycin, enacyloxin IIa, enoxacin, enrofloxacin, ertapenem, erythromycin, ethambutol, ethionamide, factumycin, fidaxomicin, fleroxacin, flomoxef, florfenicol, flucloxacillin, fluoroquinolone, fosfomycin, fosmidomycin, furazolidone, fusidic acid, ganefromycin, gatifloxacin, gentamicin, gentamicin B, gentamicin C, glycylcycline, gramicidin, gramicidin A, gramicidin B, gramicidin C, gramicidin D, gramicidin S, grepafloxacin, griseoviridin, heneicomycin, hygromycin B, iclaprim, imipenem, isepamicin, isoniazid, isopenicillin N, josamycin, kanamycin, kanamycin A, kasugamicin, kirromycin, kirrothricin, kitasamycin, levofloxacin, lincomycin, lincosamide, linezolid, lipopeptide antibiotic, lividomycin, lividomycin A, lividomycin B, lomefloxacin, loracarbef, madumycin II, mafenide, magainin, mecillinam, megalomycin, meropenem, methicillin, methicillin, methymycin, metronidazole, mezlocillin, midecamycin, minocycline, moenomycin, moenomycin A1, moxalactam, moxifloxacin, mupirocin, mycinamicin, nafcillin, nalidixic acid, narbomycin, neomycin, netilmicin, nicotinamide, niddamycin, nitrofurantoin, norfloxacin, novobiocin, ofloxacin, oleandomycin, oritavancin, ostreogrycin B3, oxacillin, oxytetracycline, para-aminosalicylic acid, paromomycin, patricin A, patricin B, pefloxacin, penam, penicillin, penicillin N, phenelfamycin A, phenelfamycin B, phenelfamycin C, phenelfamycin D, phenelfamycin E, phenelfamycin F, phenelfamycin G, phenelfamycin H, phenicol, phenoxymethylpenicillin, pikromycin, piperacillin, piperacillin-sulbactam, piperacillin-tazobactam, pleuromutilin, polymyxin, polymyxin B, polymyxin B1, polymyxin B2, polymyxin B3, polymyxin B4, pristinamycin IA, pristinamycin IB, pristinamycin IIA, propicillin, prothionamide, pulvomycin, puromycin, pyrazinamide, quinupristin, quinupristin-dalfopristin, retapamulin, rib ostamycin, rifabutin, rifampin, rifampin, rifampin, rifamycin, rifapentine, rifaximin, ristocetin, rosaramicin, roxithromycin, sisomicin, sparfloxacin, spectinomycin, spiramycin, streptogramin, streptogramin A antibiotic, streptogramin B antibiotic, streptomycin, streptothricin, sulbactam, sulfacetamide, sulfadiazine, sulfadimethoxine, sulfadimidine, sulfadoxine, sulfamethizole, sulfamethoxazole, sulfasalazine, sulfisoxazole, sulfonamide, surotomycin, synercid, tazobactam, teicoplanin, telavancin, telithromycin, temocillin, tetracycline, tetroxoprim, thiamphenicol, thiostrepton, tiamulin, ticarcillin, ticarcillin-clavulanic acid, tigecycline, tilmicosin, timentin, tinidazole, tobramycin, triclosan, trimethoprim, trimethoprim-sulfamethoxazole, trimethoprim-sulfamethoxazole, trimethoprim-sulfamethoxazole, trovafloxacin, tuberactinomycin, tulathromycin, tunicamycin, tylosin, tyrothricin, unphenelfamycin, valnemulin, vancomycin, verdamicin, vernamycin B-gamma, vernamycin C, vertilimicin, viomycin, and virginiamycin S2.

Computer Hardware and Software

The computer system for implementing the present invention can take the form of an entirely hardware embodiment, an entirely software embodiment (including firmware, resident software, microcode, etc.), or a combination of software and hardware that may all generally be referred to herein as a "circuit," "module," or "system."

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 3:
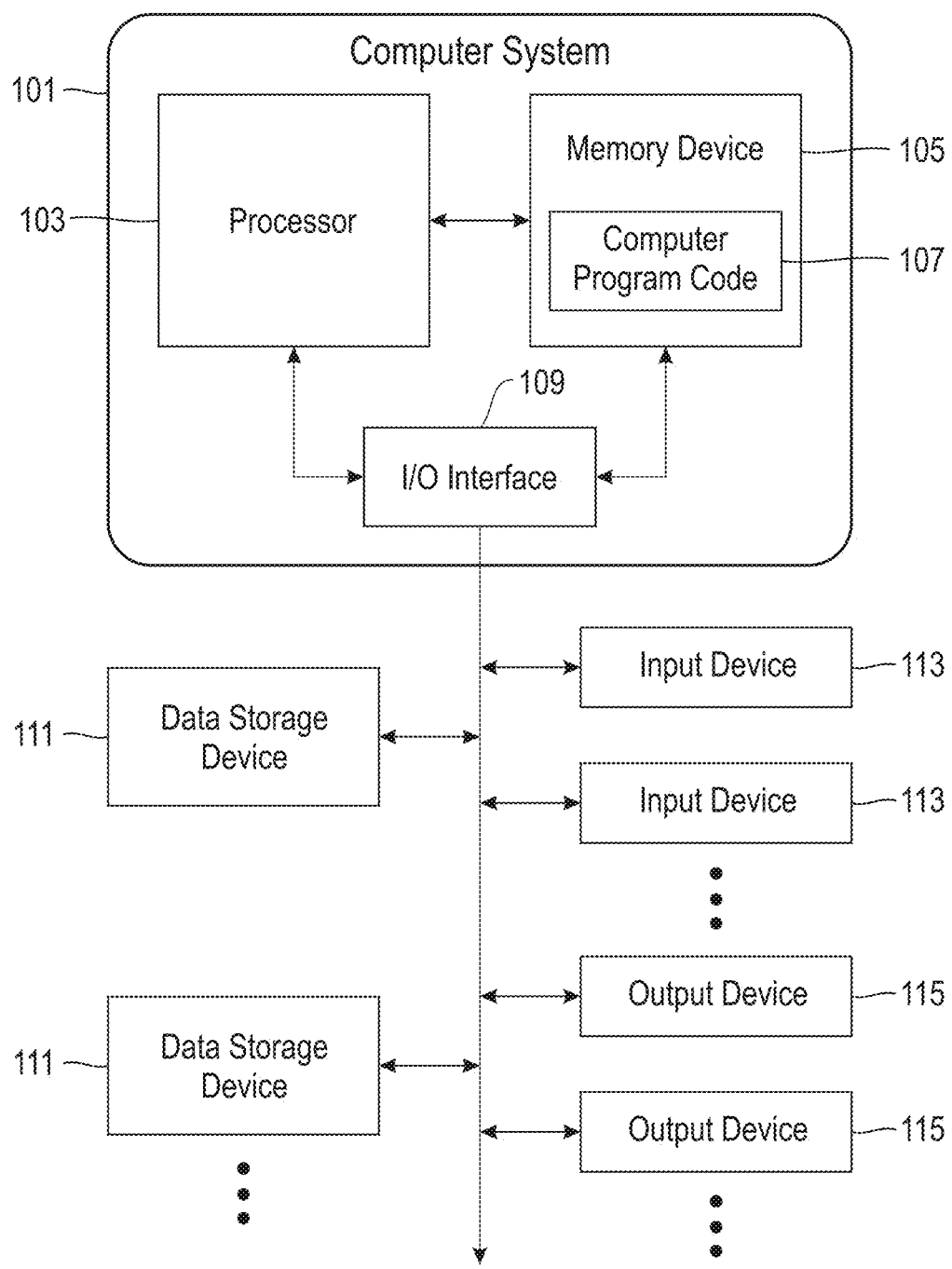
FIG. 3 is a block diagram showing the structure of a computer system and computer program code that may be used to implement the disclosed method.

FIG. 3 shows a structure of a computer system and computer program code that may be used to implement a method of processing, including natural-language processing, to perform the disclosed method. In FIG. 3, computer system 101 comprises a processor 103 coupled through one or more I/O Interfaces 109 to one or more hardware data storage devices 111 and one or more I/O devices 113 and 115. Hardware data storage devices 111 can contain, for example, the ground truth dataset(s), adjacency matrix and reconstruction matrix.

Hardware data storage devices 111 may include, but are not limited to, magnetic tape drives, fixed or removable hard disks, optical discs, storage-equipped mobile devices, and solid-state random-access or read-only storage devices. I/O devices may comprise, but are not limited to: input devices 113, such as keyboards, scanners, handheld telecommunications devices, touch-sensitive displays, tablets, biometric readers, joysticks, trackballs, or computer mice; and output devices 115, which may comprise, but are not limited to printers, plotters, tablets, mobile telephones, displays, or sound-producing devices. Data storage devices 111, input devices 113, and output devices 115 may be located either locally or at remote sites from which they are connected to I/O Interface 109 through a network interface.

Processor 103 may also be connected to one or more memory devices 105, which may include, but are not limited to, Dynamic RAM (DRAM), Static RAM (SRAM), Programmable Read-Only Memory (PROM), Field-Programmable Gate Arrays (FPGA), Secure Digital memory cards, SIM cards, or other types of memory devices.

At least one memory device 105 contains stored computer program code 107, which is a computer program that comprises computer-executable instructions. The stored computer program code can include a program for natural-language processing that implements the disclosed methods. The data storage devices 111 may store the computer program code 107. Computer program code 107 stored in the storage devices 111 can be configured to be executed by processor 103 via the memory devices 105. Processor 103 can execute the stored computer program code 107.

Thus the present invention discloses a process for supporting computer infrastructure, integrating, hosting, maintaining, and deploying computer-readable code into the computer system 101, wherein the code in combination with the computer system 101 is capable of performing the disclosed methods.

Any of the components of the present invention could be created, integrated, hosted, maintained, deployed, managed, serviced, supported, etc. by a service provider. Thus, the present invention discloses a process for deploying or integrating computing infrastructure, comprising integrating computer-readable code into the computer system 101, wherein the code in combination with the computer system 101 is capable of performing the disclosed methods.

One or more data storage units 111 (or one or more additional memory devices not shown in FIG. 3) may be used as a computer-readable hardware storage device having a computer-readable program embodied therein and/or having other data stored therein, wherein the computer-readable program comprises stored computer program code 107. Generally, a computer program product (or, alternatively, an article of manufacture) of computer system 101 may comprise said computer-readable hardware storage device.

While it is understood that program code 107 may be deployed by manually loading the program code 107 directly into client, server, and proxy computers (not shown) by loading the program code 107 into a computer-readable storage medium (e.g., computer data storage device 111), program code 107 may also be automatically or semi-automatically deployed into computer system 101 by sending program code 107 to a central server (e.g., computer system 101) or to a group of central servers. Program code 107 may then be downloaded into client computers (not shown) that will execute program code 107.

Alternatively, program code 107 may be sent directly to the client computer via e-mail. Program code 107 may then either be detached to a directory on the client computer or loaded into a directory on the client computer by an e-mail option that selects a program that detaches program code 107 into the directory.

Another alternative is to send program code 107 directly to a directory on the client computer hard drive. If proxy servers are configured, the process selects the proxy server code, determines on which computers to place the proxy servers' code, transmits the proxy server code, and then installs the proxy server code on the proxy computer. Program code 107 is then transmitted to the proxy server and stored on the proxy server.

In one embodiment, program code 107 is integrated into a client, server and network environment by providing for program code 107 to coexist with software applications (not shown), operating systems (not shown) and network operating systems software (not shown) and then installing program code 107 on the clients and servers in the environment where program code 107 will function.

The first step of the aforementioned integration of code included in program code 107 is to identify any software including the network operating system (not shown), which is required by program code 107 or that works in conjunction with program code 107 and is on the clients and servers where program code 107 will be deployed. This identified software includes the network operating system, where the network operating system comprises software that enhances a basic operating system by adding networking features. Next, the software applications and version numbers are identified and compared to a list of software applications and correct version numbers that have been tested to work with program code 107. A software application that is missing or that does not match a correct version number is upgraded to the correct version.

A program instruction that passes parameters from program code 107 to a software application is checked to ensure that the instruction's parameter list matches a parameter list required by the program code 107. Conversely, a parameter passed by the software application to program code 107 is checked to ensure that the parameter matches a parameter required by program code 107. The client and server operating systems, including the network operating systems, are identified and compared to a list of operating systems, version numbers, and network software programs that have been tested to work with program code 107. An operating system, version number, or network software program that does not match an entry of the list of tested operating systems and version numbers is upgraded to the listed level on the client computers and upgraded to the listed level on the server computers.

After ensuring that the software, where program code 107 is to be deployed, is at a correct version level that has been tested to work with program code 107, the integration is completed by installing program code 107 on the clients and servers.

Embodiments of the present invention may be implemented as a method performed by a processor of a computer system, as a computer program product, as a computer system, or as a processor-performed process or service for supporting computer infrastructure.

The computer system, the computer program product, and/or the service can be located at a cloud platform. The computer product can identify differences between entries of the reconstruction matrix and corresponding entries of the adjacency matrix and provide a report of the identified differences to a user. When an entry value in the input adjacency matrix is 0 and the same entry in the reconstructed adjacency matrix is greater than 0, the entry value of the reconstructed adjacency matrix can be interpreted as the score of the predicted association between the respective biosample (row index) and metadata instance (column index). The prediction scores can be ranked by their values and thresholded in order to identify and select the most relevant predictions, which are then output to a user.

EXAMPLES

The following example demonstrates prediction of antimicrobial resistance using matrix factorization. The antibiogram and associated metadata were put in matrix form, the parameters of matrix factorization were determined (i.e., the number of the latent factors), Matrix factorization of the initial association matrix was performed and then a new association matrix was constructed containing predictions of associations between sample isolates and antibiotics. In this example, the isolates are referred to by the genus. Four genera were studied: *Salmonella, Campylobacter, Shigella,* and *Escherichia.*

Data

Data were downloaded from the National Antimicrobial Resistance Monitoring System (NARMS) of the Centers for Disease Control (CDC) at the website formed by the concatenation of "https://wwwn" and ".cdc.gov/narmsnow/".

Plotting

Tabulations of the NARMS data were performed in python using the pandas package. All plots were made with using either R (libraries: ggplot2 (at the website formed by the concatenation of "https://" and "cran.r-project.org/package=ggplot2") and fiftystater (at the website formed by the concatenation of "https://" and "CRAN.R-project.org/package=fiftystater")) or python (packages: matplotlib (at the website formed by the concatenation of "https://" and "matplotlib.org/") and Seaborn (at the website formed by the concatenation of "https://" and "seaborn.pydata.org/")). Construction of the network representation of the NARMS data was performed using python igraph package. Network visualization and modularity analysis were performed using Gephi software (at the website formed by the concatenation of "https://" and "gephi.org/")).

Matrix Factorization (MF)

Matrix factorization is a class of algorithms used in recommendation systems for its scalability and accuracy. MF algorithms work by factorizing the data matrix into two latent feature matrices of low dimensions that can be used to reconstruct the initial data matrix. For a data matrix representing the resistance/susceptibility of the isolates against antibiotics, MF learns two latent feature matrices, one for isolates and the other for antibiotics. Each row of the isolates latent feature matrix is the feature vector, u learned for the corresponding isolate i. And each row of the antibiotics latent feature matrix represents the feature vector, $v_j$, for antibiotic j. From these learned feature vectors, resistance phenotype of an isolate i against an antibiotic j can be predicted by taking the dot product of the respective feature vectors, $\hat{r}_{ij} = u_i \cdot v_j$.

In general, matrix factorization algorithms learn latent features based on the known resistance/susceptible phenotypes present in the data matrix and do not require any additional metadata of the isolates or antibiotics. The concept behind MF is that there are certain properties of isolates and antibiotics that explain the interactions present in the data matrix, and the latent features learned by MF represent them. These latent features for an isolate could be simple and interpretable features such as genus or species of the bacteria to something much more complex such as the presence of certain genes. Similarly, for an antibiotic, the latent features could be the class of antibiotics or the presence of certain molecular attributes of the antibiotic. For applying matrix factorization algorithms, the antimicrobial resistance data of m isolates and n antibiotics is represented as a matrix, $R \in \mathbb{R}^{m \times n}$, where Rij=1 if isolate i is susceptible against antibiotic j, Rij=−1 if isolate i is resistant against antibiotic j, and Rij=0 if isolate i has unknown resistance against antibiotic j.

The matrix factorization learns latent feature vectors for isolates (u) and antibiotics (v) by minimizing following objective function:

$$J = \Sigma_{i,j \in R_K}(R_{ij} - u_i^T v_j)^2 + \lambda(\|u_i\|^2 + \|v_j\|^2) \qquad (1),$$

where $R_K$ is the pair of isolates and antibiotics with resistance/susceptible phenotype known, and λ is the regularization parameter used to avoid overfitting while learning latent feature vectors. Different matrix factorization algorithms are defined based on the objective function, restrictions applied on feature vectors, and learning algorithms used for optimization.

In this work, four widely used matrix factorization algorithms were used:

i) Matrix Factorization with Alternating Least Squares (ALS). This is a basic matrix factorization with the objective function defined in equation 1 and alternating least squares approach used for optimization.

ii) Matrix Factorization with Implicit Feedback (ALS Implicit). Matrix factorization algorithms for recommendation systems mostly work on explicit feedback data available, such as the ratings users give to movies. Instead of this, MF with implicit feedback factorizes implicit feedback derived from the explicit data along with a confidence score obtained from the explicit feedback by minimizing the following objective function:

$$J = \Sigma_{i,j} c_{ij}(p_{ij} - u_i^T v_j)^2 + \lambda(\Sigma_i \|u_i\|^2 + \Sigma_j \|v_j\|^2) \qquad (2),$$

where $p_{ij}$ is the implicit feedback and $c_{ij}$ is the confidence score.

iii) Nonnegative Matrix Factorization (NMF). NMF is a matrix factorization algorithm which has a constraint that the data matrix and latent feature vectors are nonnegative.

iv) Matrix Factorization with Weighted Approximate-Rank Pairwise loss (MF-WARP). The loss functions in traditional MF algorithms do not focus on the relative order between the predicted value of two antibiotics against an isolate. A weighted approximate-rank pairwise (WARP) loss function learns latent factors such that the relative order of the predicted value between antibiotics against an isolate is preserved.

For ALS and ALS Implicit, the implementation from Apache Spark was used. Scikit-learn was used for NMF. Lightfm was used for MF-WARP.

Evaluation

To benchmark the performance of various matrix factorization algorithms, the following metrics are used:

i) Area Under ROC/PR curve. For each isolate in the test data, the resistance/susceptibility phenotype value for all antibiotics was predicted except the ones present in the training data. Susceptible isolate-antibiotic pairs present in test data were labeled as 1, and the rest of the isolate-antibiotic pairs were labeled as 0. From this, the Area Under ROC curve (AUROC) and Area Under PR curve (AUPR) were calculated for each isolate. The mean and standard deviation of AUROC and AUPR values were calculated for all isolates in the test data. AUCROC and AUCPR measures the accuracy of binary classification, and here these metrics will measure how well the model can classify susceptible antibiotic and resistant antibiotics. While both AUCROC and AUCPR provide similar information for class balanced data, AUCPR is more suitable for class imbalanced data. Only 8% of the data were resistant. Therefore, AUCPR will be more useful than AUCROC while measuring the performance of resistant isolate-antibiotic pairs prediction.

ii) Precision @k. For each isolate in the test data, antibiotics which are not present in the training data were ordered based on the predicted phenotype value. From these ordered antibiotics, the top k antibiotics were selected, where k is a positive integer. A precision score was then calculated as follows: Precision @k=(Number of susceptible isolate-antibiotic pairs in top k)/k. Precision @k measures the quality of the top k recommendations. In this case, it measures how accurately a model can predict the top k susceptible/resistant isolate-antibiotic pairs.

iii) Root Mean Squared Error (RMSE). For all pairs of isolates and antibiotics in the test data, the phenotype value was predicted and the RMSE calculated. RMSE measures how well the model can reconstruct the initial data matrix. All these metrics are calculated for predicting susceptible and resistant antibiotics.

Results

Data Characterization

Figure 4A:
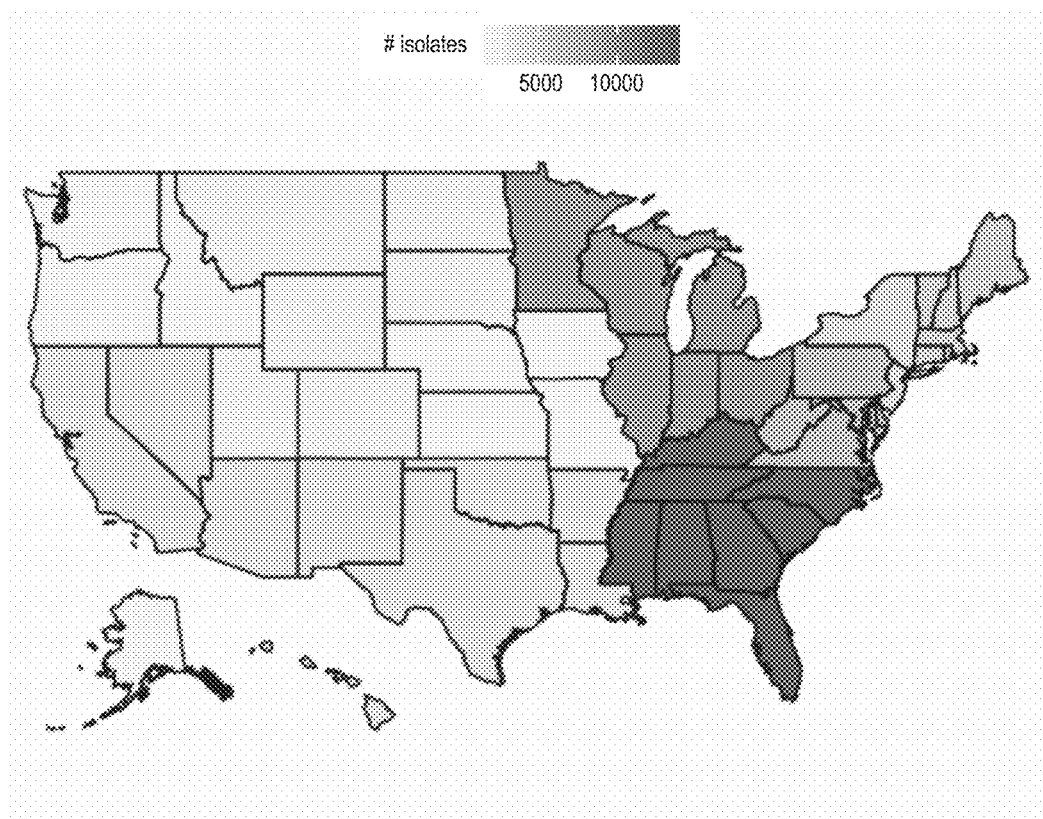
FIGS. 4A-4D are graphs characterizing NARMS CDC patient data, respectively, by i) the number of isolates per region in the USA (FIG. 4A), ii) the number of isolates tested per genus over time (FIG. 4B), iii) distribution of age-ranges of patients for the isolates (FIG. 4C), and iv) distribution of isolation sources (FIG. 4D).
Figure 4B:
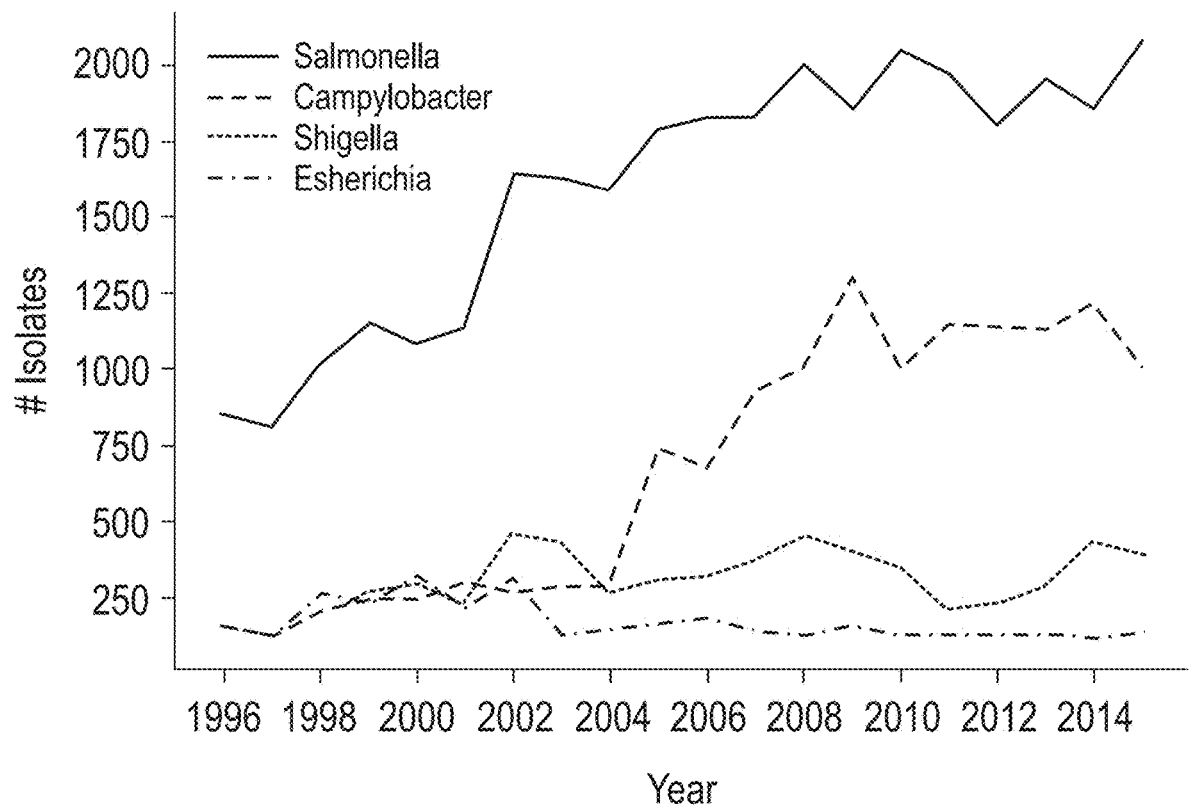
Figure 4C:
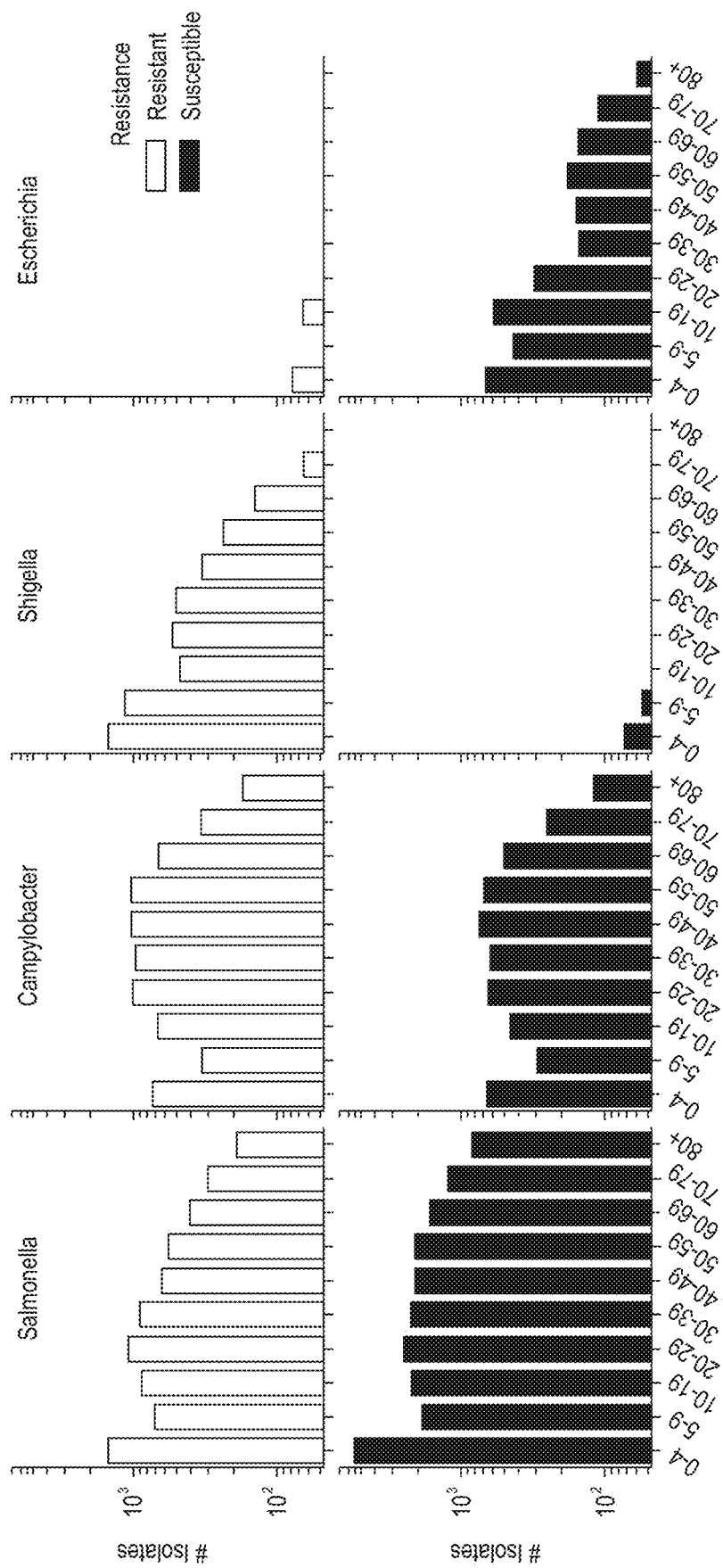
Figure 4D:
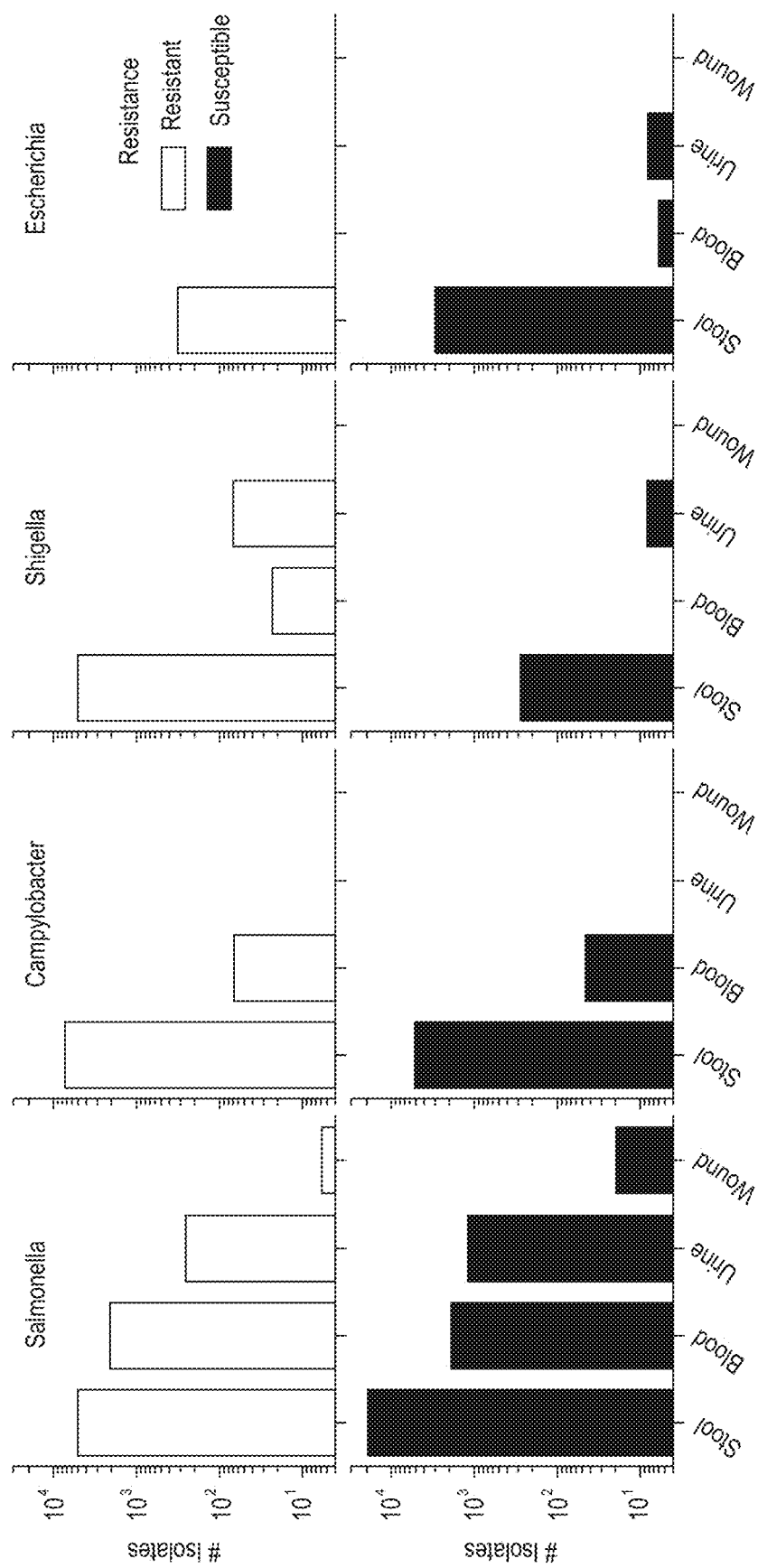
Figure 5B:
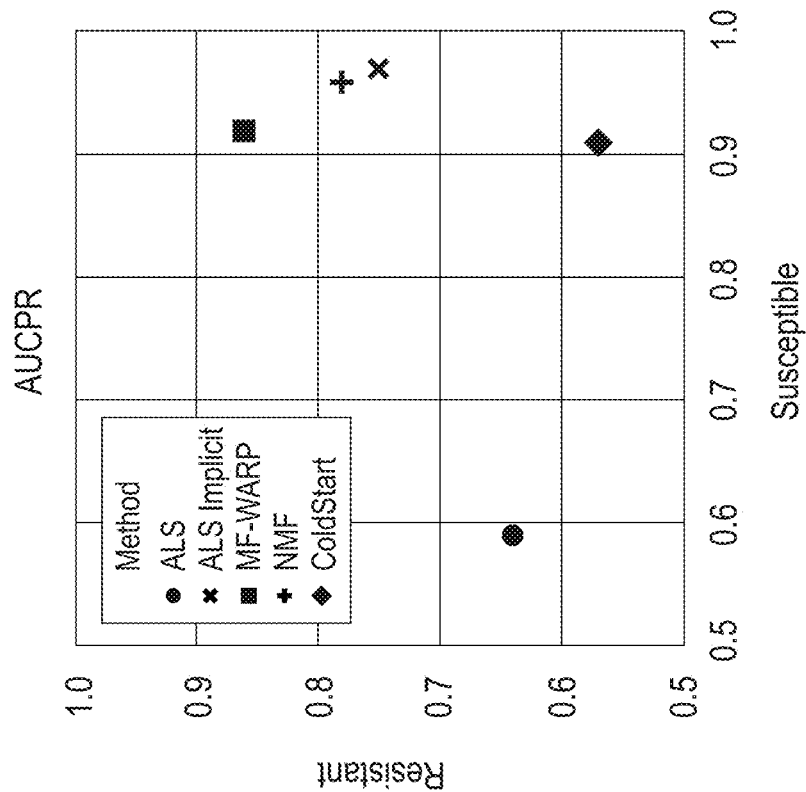
FIGS. 5A-5D are scatter plots showing the area under the ROC (AUCROC) and PR (AUCPR) curves, Precision @3, and RMSE results, respectively, for various matrix factorization approaches on all-genera antibiograms. Predictions of the resistant and susceptible classes were performed separately.
Figure 5A:
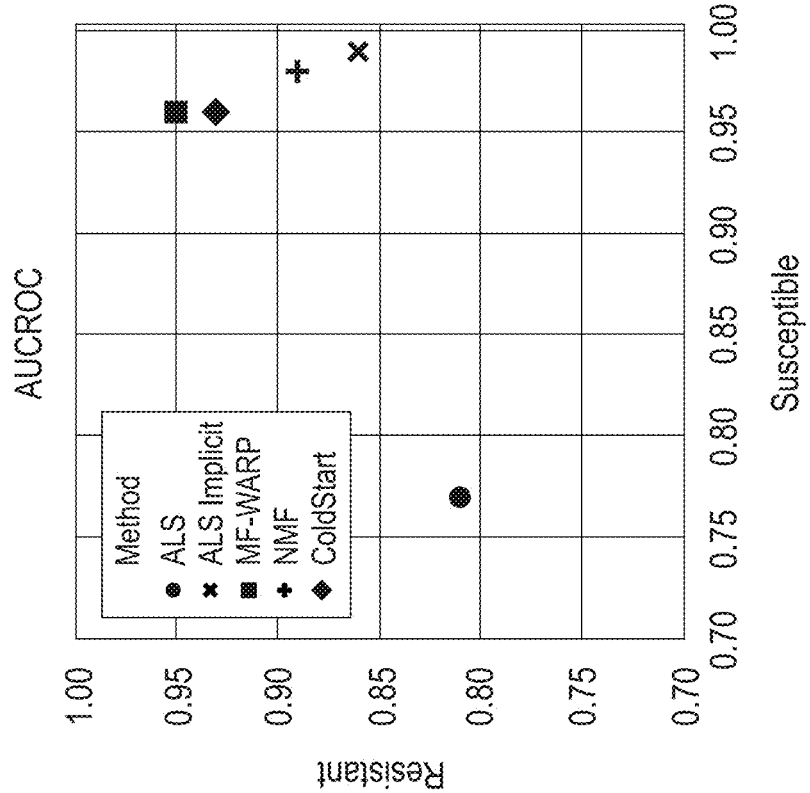
Figure 5D:
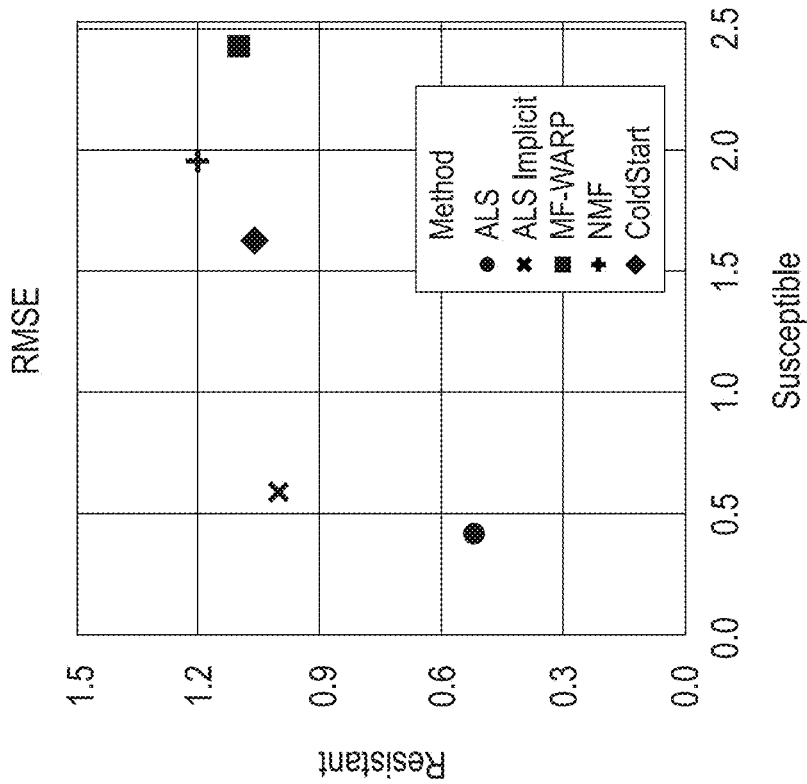
Figure 5C:
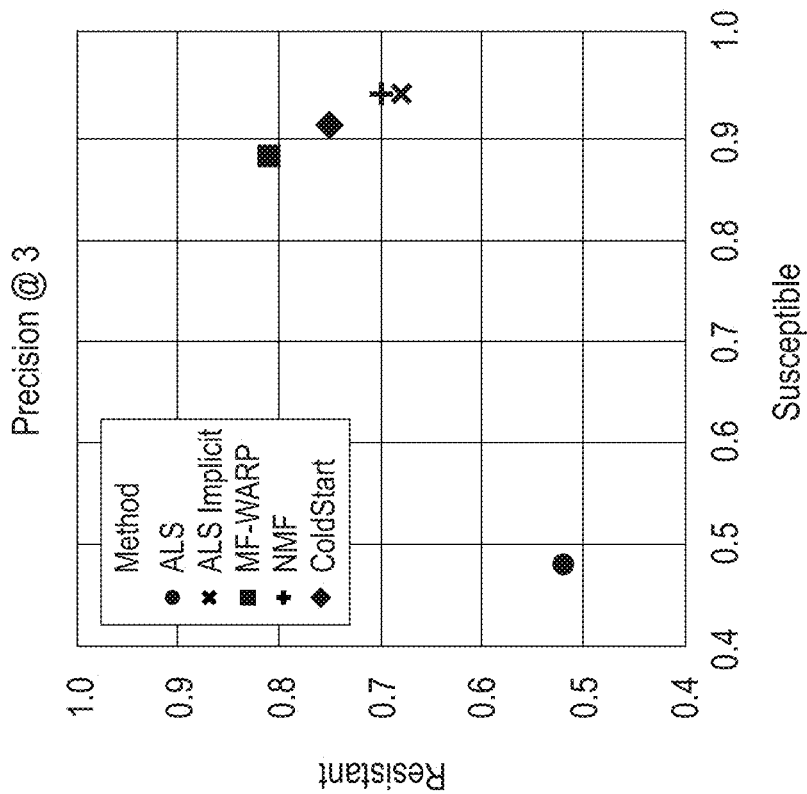
Figures 6A, 6B:
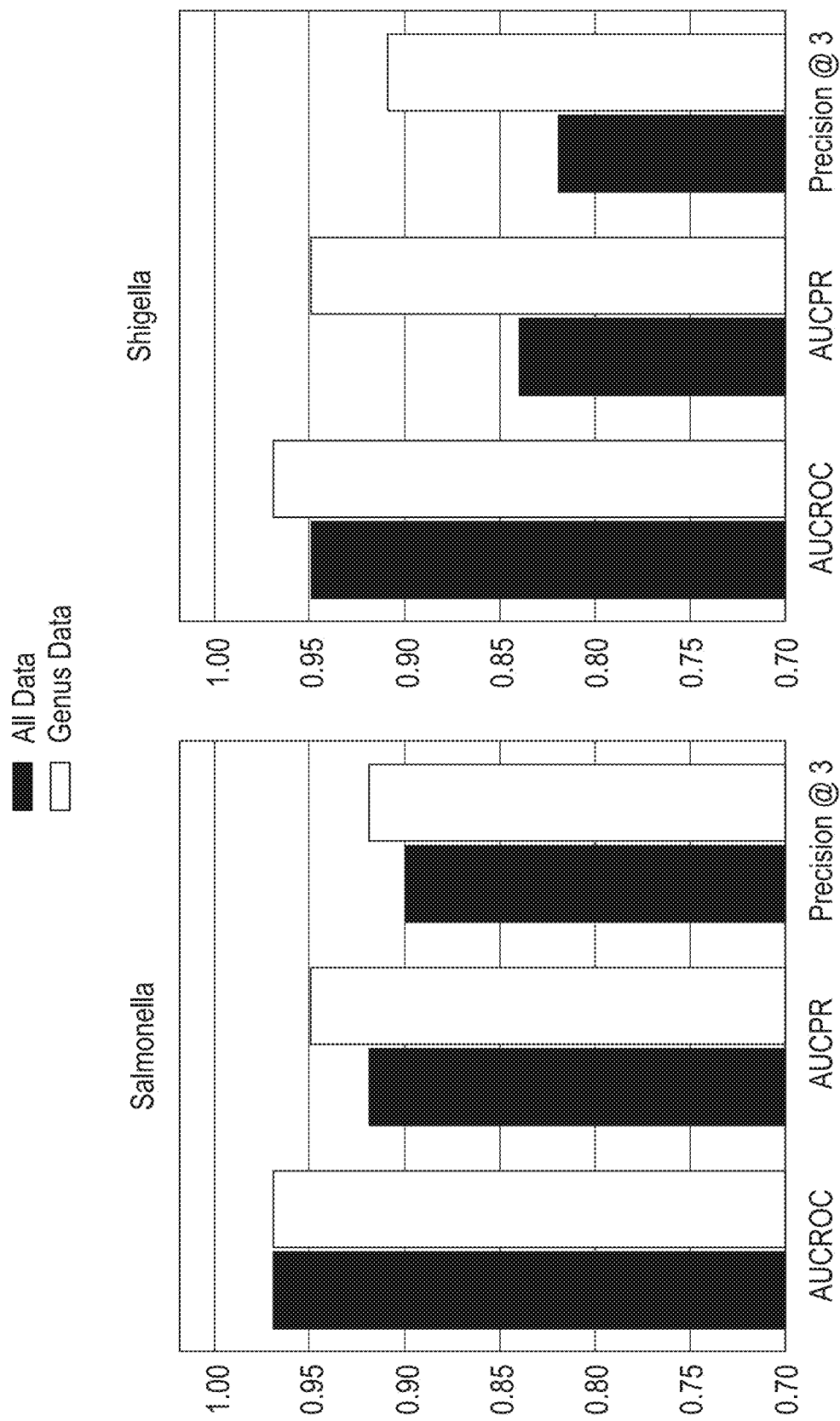
FIGS. 6A-6D are bar graphs showing the areas under the ROC, PR curves, and Precision @3 results obtained with MF-WARP for predicting susceptibility of *Salmonella, Shigella, Escherichia*, and *Campylobacter* to antibiotics. Genus only data and complete data are shown.
Figures 6C, 6D:
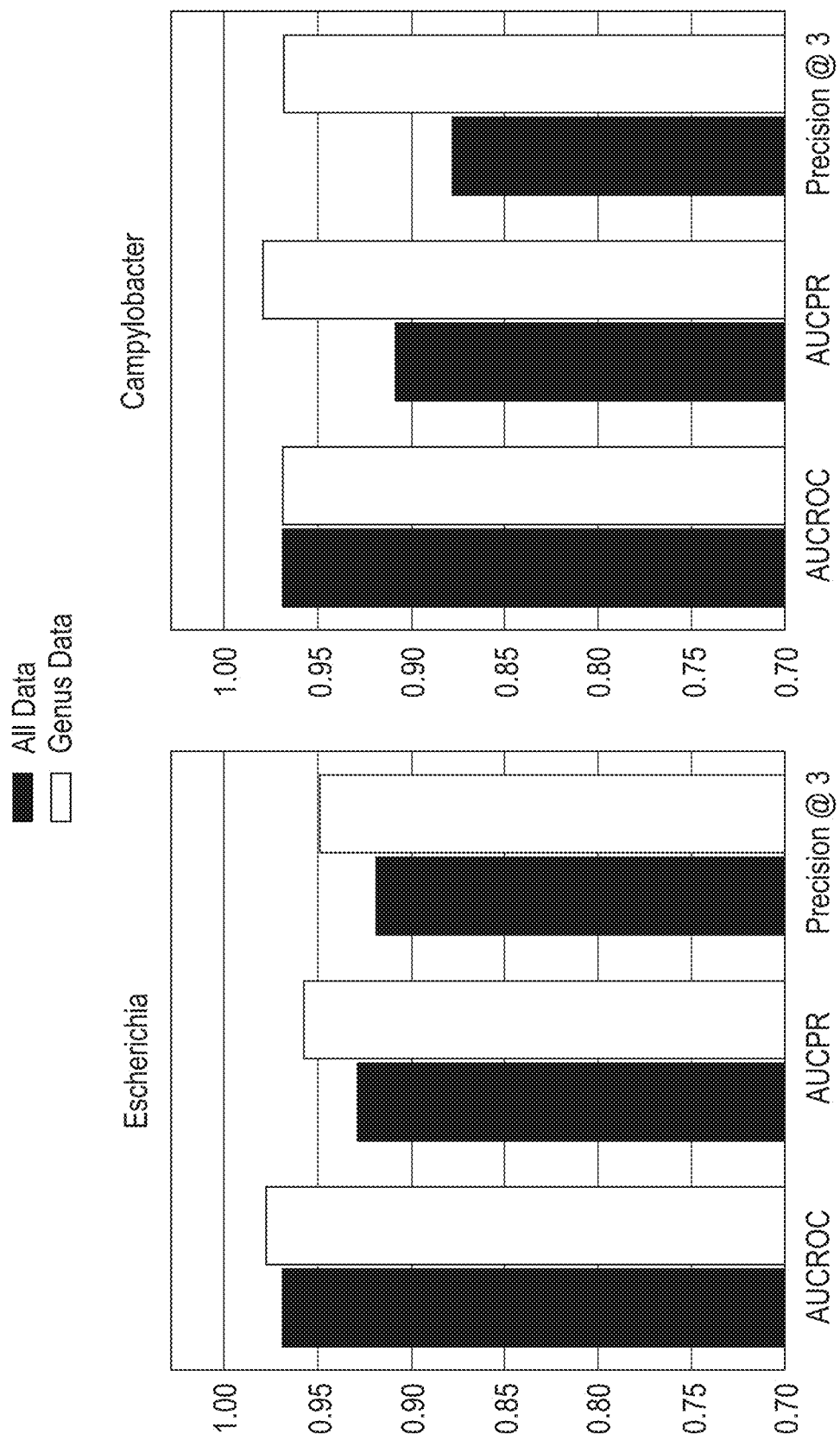
Figures 6E, 6F:
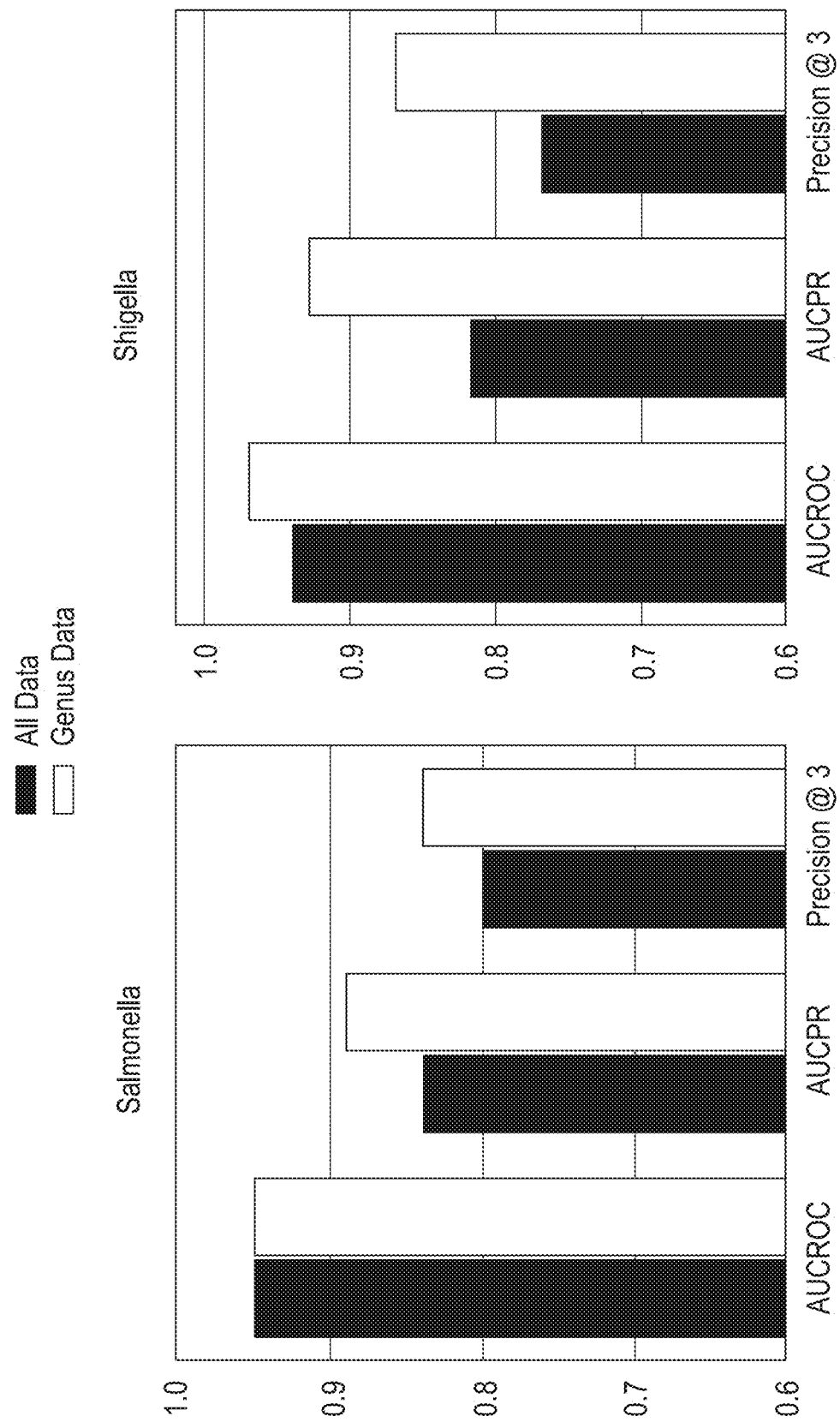
FIGS. 6E-6H are bar graphs showing the areas under the ROC, PR curves, and Precision @3 results obtained with MF-WARP for predicting resistance of *Salmonella, Shigella, Escherichia*, and *Campylobacter* genera to antibiotics. Genus only data and complete data are shown.
Figures 6G, 6H:
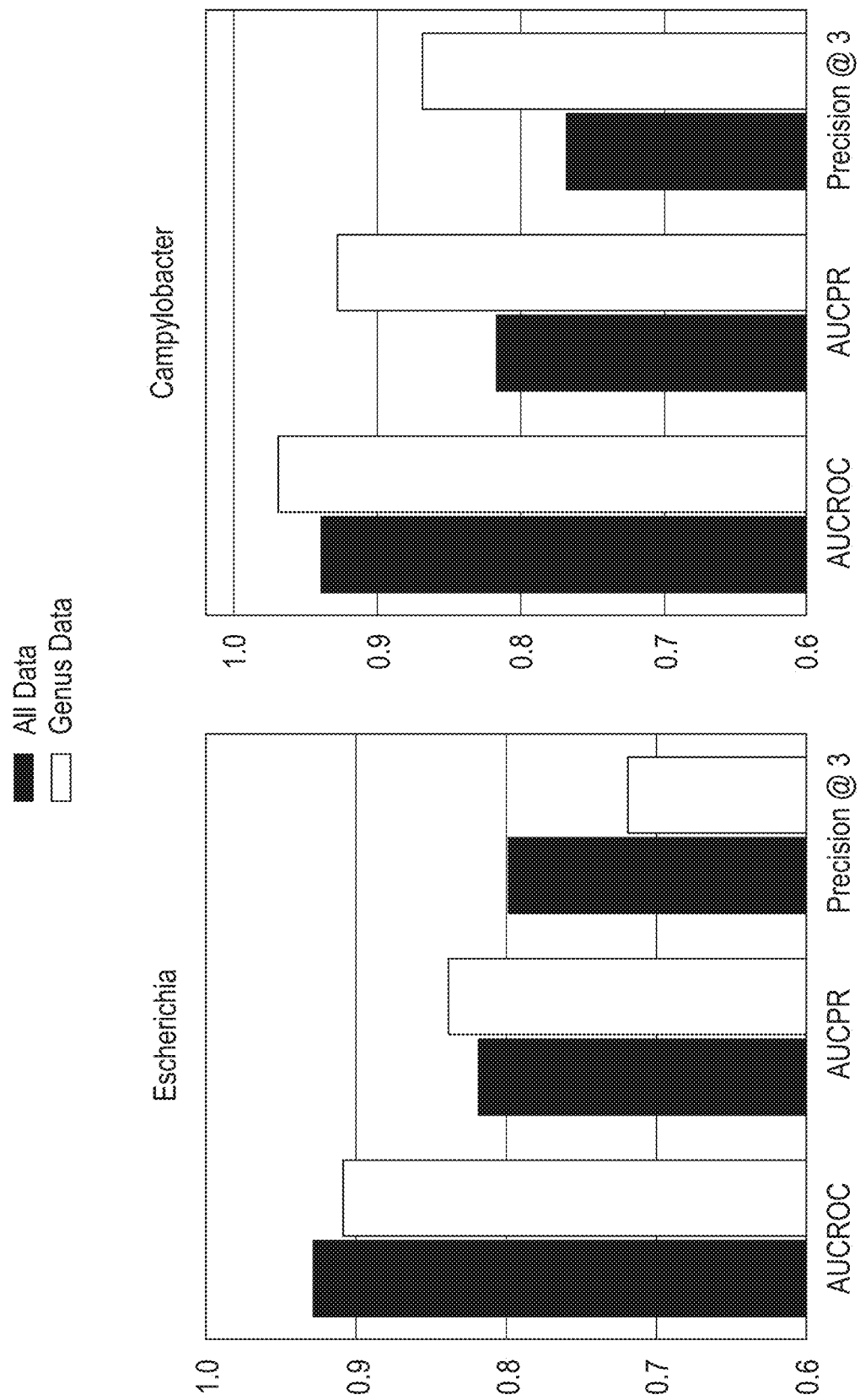

NARMS has generated human isolate data from 1996 to 2015 including metadata such as the classification, antibiotic susceptibility results, site of isolation, year of specimen collection, region, and age category. Four genera are monitored by NARMS: *Salmonella, Campylobacter, Shigella*, and *Escherichia*, which in total covers 8 species and over 400 serovars of *Salmonella*. FIGS. 4A-4D characterize NARMS CDC patient data, respectively, by i) the number of isolates per region in the USA (FIG. 4A), ii) the number of isolates tested per genus over time (FIG. 4B), iii) distribution of age-ranges of patients for the isolates (FIG. 4C), and iv) distribution of isolation sources for the isolates (FIG. 4D). Each of these features or combination of them has the potential to reveal patterns of susceptibility/resistance of the antibiotics tested.

With respect to Region, isolate collection is biased towards the Eastern and Southeastern regions of the United States. With respect to Genus, monitoring is heavily biased towards *Salmonella* and *Campylobacter*. With respect to Age Range, for each genus there is a moderate bias towards isolates and younger patients for *Salmonella, Shigella*, and *Escherichia*, but not for *Campylobacter*. It is also clear that the majority of *Shigella* cases skew towards having resistance to at least one tested antibiotic, while *Escherichia* cases skew towards complete susceptibility. With respect to Isolation Source, for many of the isolates, the source of isolation is included. Four of the listed sources are Stool, Urine, Blood, and Wounds. There were very few cases of other classified metadata in the dataset. With respect to Resistance Phenotype of an antibiotic, this is represented using three states: R (Resistant), S (Susceptible) and X (Inconclusive). For matrix factorization (MF), only R and S entries in the data were considered.

Data Clustering

For the purposes of MF analysis the data are represented as an adjacency matrix between isolates and antibiotic. The data showed clustering of the isolate-antibiotic pairs into three identified communities: Cluster I is composed primarily of *Campylobacter* (*Campylobacter* 71%, *Salmonella* 14%, *Shigella* 14%), Cluster II is primarily *Salmonella* (*Salmonella* 79%, *Shigella* 20%), and Cluster III is primarily *Salmonella* (*Salmonella* 82%, *Shigella* 9%, *Escherichia* 9%). The association of antibiotics with the clusters is as follows:

Cluster I—AZM,CIP,CLI,ERY,FFN,GEN,NAL,TEL;

Cluster II—ATM,CAZ,CTX,FEP,IMI,PTZ; and

Cluster III—AMI, AMP, AUG, AXO, CEP, CHL, COT, FIS, FOX, CAM, SMX, STR, TET, TIO.

Table 4 lists the names of the drugs associated with the above acronyms.

TABLE 4

| | |
|---|---|
| AMI | Amikacin |
| AMP | Ampicillin |
| ATM | Aztreonam |
| AUG | Amoxicillin-clavulanic acid |
| AXO | Ceftriaxone |
| AZM | Azithromycin |
| CAM | Chloramphenicol |
| CAZ | Ceftazidime |
| CEP | Cephalothin |
| CHL | Chloramphenicol |
| CIP | Ciprofloxacin |
| CLI | Clindamycin |
| COT | Trimethoprim-sulfamethoxazole |
| CTX | Cefotaxime |
| ERY | Erythromycin |
| FEP | Cefepime |
| FFN | Florfenicol |
| FIS | Sulfisoxazole |
| FOX | Cefoxitin |
| GEN | Gentamicin |
| IMI | Imipenem |
| NAL | Naladixic acid |
| PTZ | Piperacillin-tazobactam |
| SMX | Sulfamethoxazole |
| STR | Streptomycin |
| TEL | Telithromycin |
| TET | Tetracycline |
| TIO | Ceftiofur |

Matrix Factorizations

The performance of the above-listed MF algorithms in predicting antimicrobial resistance of an isolate were benchmarked. The MF algorithms were selected such that each of them had distinctive features: unconstrained alternating least squares (ALS), nonnegative matrix factorization (NMF), implicit feedback (ALS-Implicit), and ranking based (a matrix factorization model that optimizes the weighted approximately ranked pairwise ranking loss (MF-WARP)).

The hypothesis generation task solved by MF-based recommender was formulated as follows. For a given uncharacterized pair isolate-antibiotic, the goal was to predict the isolate class as "resistant" or "susceptible". To this end, the initial NARMS dataset was transformed into two adjacency matrices between isolates and antibiotics. One matrix ("susceptible" class) was given high weightage for susceptible entries and low weightage for resistant entries. The other matrix ("resistant" class) was given high weightage for resistant entries and low weightage for susceptible entries.

The adjacency matrix for the susceptible class was constructed in the following manner:

ALS/ALS Implicit/MF-WARP: 1 (susceptible), −1 (resistant) and 0 (unknown);

NMF: 5 (susceptible), 1 (resistant) and 0 (unknown).

The adjacency matrix for the resistant class was constructed in the following manner:

ALS/ALS Implicit/MF-WARP: 1 (resistant), −1 (susceptible), and 0 (unknown);

NMF: 5 (resistant), 1 (susceptible) and 0 (unknown).

These association matrices were subject to MF analysis separately, so that for a given pair isolate-antibiotic one MF model generated the hypothesis that the pair is "susceptible" and the other model generated the hypothesis that the pair is "resistant". This approach also proved helpful in gaining insights into the severity of the class imbalances problem in NARMS data: 92% of the available data are in the "susceptible" class and only 8% are in the "resistant" class. Since the data are imbalanced having very few antibiotics in the resistant group, this approach helps to address underfitting and predict antimicrobial resistance with better accuracy. An MF model learned for predicting susceptible isolate-antibiotic pairs need not be the best one for predicting resistant isolate-antibiotic pairs. Also, ranking based algorithms such as MF-WARP work by improving the prediction accuracy for one class. Separate association matrix and models for predicting resistant and susceptible isolate-antibiotic pairs makes more sense for such algorithms.

Five-fold cross validation was used for parameter selection. Five-fold cross validation is performed by randomly partitioning known isolate-antibiotic pairs into five folds of equal size. After partitioning, the MF model is trained on four folds and tested on the remaining one fold. This is repeated five times such that each of the folds will be used exactly one time for testing. Five-fold cross validation was then repeated three times on different random partitions.

Cold Start. MF requires some pre-existing information about isolate resistant/susceptible phenotype in order to predict new phenotypes. The situation when there is no such information available (i.e., no antibiotics have been tested against a particular isolate) is referred to as a cold start problem. In order to resolve this problem, phenotypes of uncharacterized isolates were inferred from the phenotypes of the most similar isolates. Isolate similarity was evaluated from the metadata, such as genus, species, serotype, age group, geographic region, and year: available metadata were vectorized using one-hot encoding, distances between isolates were evaluated as Euclidean distances, and the predictions for the phenotype of the isolates causing cold start problem was generated as a linear combination of the prediction often nearest isolates. Cold start experiments were performed based on the best performing matrix factorization model from previous experiment with 5-fold cross validation.

All-genera vs genus-specific antibiograms. It is unclear how the presence of multiple genera in the compiled antibiogram data impacts predictions of antibiotic resistance produced by the recommender system. In order to address this question genus-specific datasets were prepared. The recommender system performances of all-genera and genus-specific cases were then benchmarked.

The performance of various matrix factorization approaches for predicting susceptible and resistant isolate-antibiotic pairs is summarized in FIGS. 5A-5D. ALS Implicit and NMF performed better than the other algorithms when predicting susceptible isolate-antibiotic pairs, indicated by the area under the receiver operating characteristic curve (AUCROC) of 0:98, the area under the precision recall curve (AUCPR) of 0:96, and Precision @3 of 0:94. MF-WARP gave slightly less accuracy when predicting susceptible isolate-antibiotic pairs with AUCROC of 0:96, AUCPR of 0:92, and Precision @3 of 0:88. When predicting resistant isolate-antibiotic pairs, MF-WARP clearly outperformed the other algorithms with AUCROC of 0:95, AUCPR of 0:86, and Precision @3 of 0:81. Overall, MF-WARP gave better results in predicting both susceptible and resistant isolate-antibiotic pairs compared to the other algorithms. Cold start results based on MF-WARP are also shown in FIGS. 5A-5D. Cold start results were comparable to MF-WARP results for predicting susceptible and resistant isolate-antibiotic pairs.

Figure 7A:
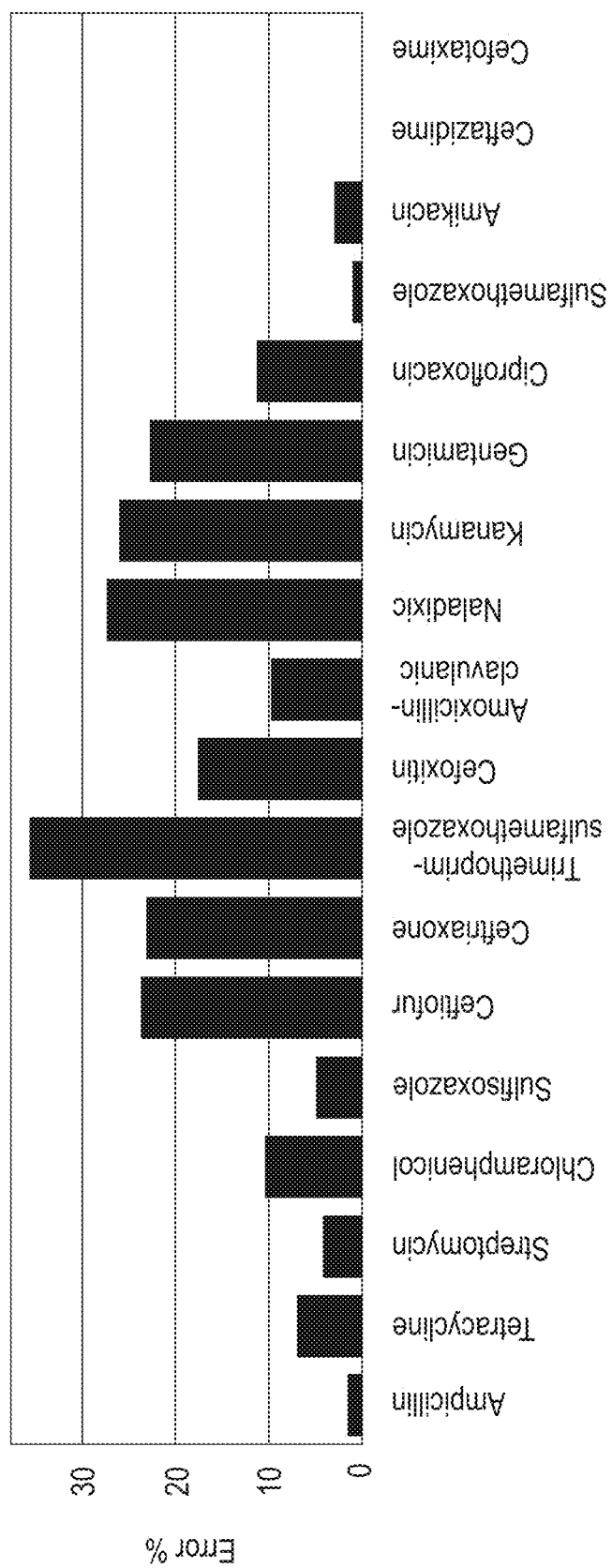
FIGS. 7A-7B are bar graphs showing the error rate in predicting microbial resistance to antibiotics using MF-WARP.
Figure 7B:
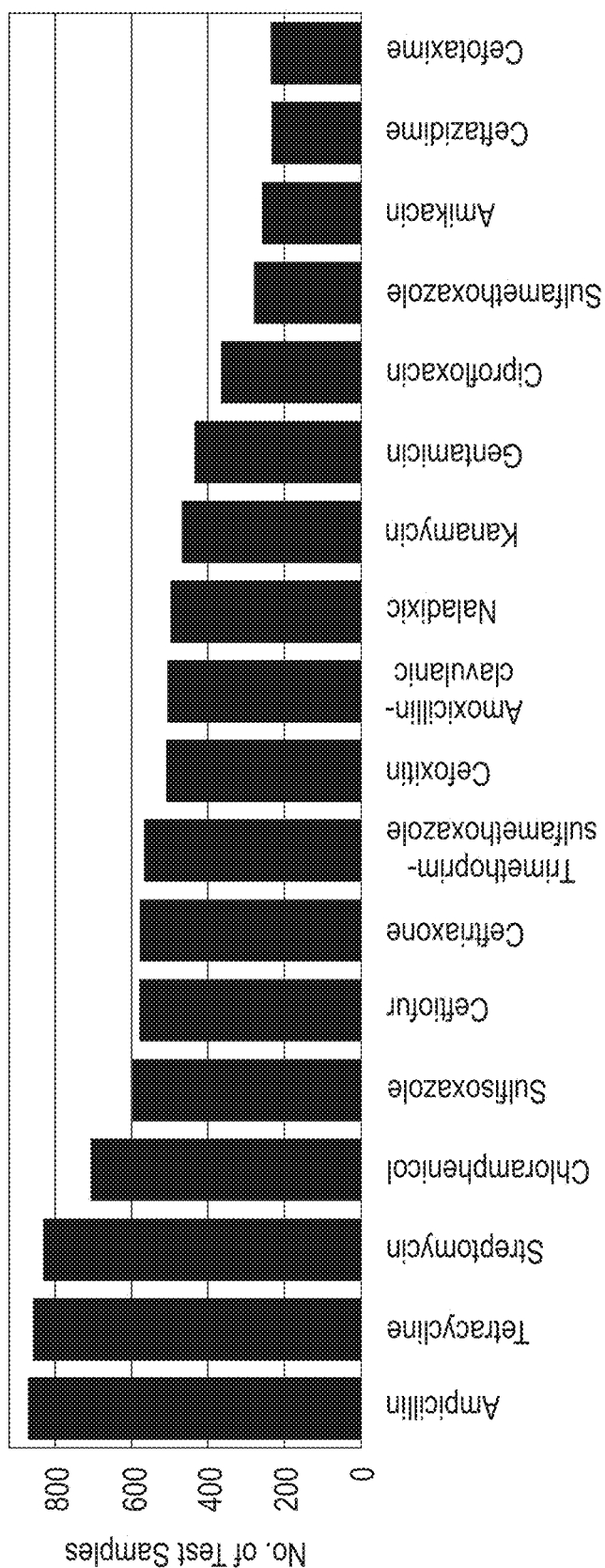

The MF-WARP performance was evaluated in all-genera and genus-specific (*Salmonella, Shigella, Eschetichia,* and *Campylobacter*) recommendation tasks. The performance metrics for prediction of susceptible genus-antibiotic pairs are shown in FIGS. 6A-6D. The performance metrics for prediction of resistant genus-antibiotic pairs are shown in FIGS. 6E-6H. Genus-specific performance was higher than the all-genera performance for the prediction of both susceptible and resistant genus-antibiotic pairs in the case of all four genera. FIGS. 7A-7B (bar graphs) show the error rates for predicting resistant isolate-antibiotic pairs for 18 different antibiotics using MF-WARP. FIG. 7A shows the error obtained for each drug. FIG. 7B shows the number of test samples for each drug.

DISCUSSION

Predicting a "resistant" phenotype is more important than predicting a "susceptible" phenotype from both statistical and clinical perspectives. The former is the case because the data are heavily skewed towards susceptible phenotype. The latter is the case because making a false negative prediction about resistivity of an isolate to an antibiotic is far more harmful than making a false positive prediction about susceptibility of the isolate, given a larger fraction of susceptible isolates in the dataset. Benchmarking results show a high area under PR curve (AUCPR) in predictions of "susceptible" and "resistant" phenotypes. Among the four versions of MF, MF-WARP showed the most consistent results in predictions of each phenotype. Considering significant imbalance in the data between these phenotypes, it is highly encouraging that MF showed little sensitivity to the imbalance. Another type of imbalance is associated with the taxonomic identity of isolates: the largest represented genus, *Salmonella*, comprises 58.7% of the isolates, whereas the smallest represented genus, *Escherichia*, comprises 6.3%. In order to explore how the composition of the data in regards to genera affects the performance of prediction, MF was performed on the combined dataset and each genus separately. Genus specific data was found to outperform combined data in the prediction of "resistant" phenotype, particularly for *Shigella* and *Campylobacter*. This result also shows that the size of the dataset, in this case restricted to individual genera, is not a driver for the MF performance because *Shigella* and *Campylobacter* are not the most abundant classes. A possible explanation for *Campylobacter* is its distinct antibiotic profile, an observation further supported by the distinct clustering of *Campylobacter*. High-quality predictions were obtained with 3 latent factors (age group, data year, and region name). A separate analysis is required to provide interpretation of these latent factors.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A method, comprising: providing an initial matrix comprising rows corresponding to microorganisms and columns corresponding to metadata associated with one or more of the microorganisms, the metadata including antibiogram data, wherein an element of the initial matrix linking a microorganism to an antibiotic drug has a numerical value indicating no antibiogram data exist for the microorganism with respect to the antibiotic drug; factoring the initial matrix using a matrix factorization algorithm, thereby forming a first factor matrix and a second factor matrix, wherein training data is used to train the matrix factorization algorithm, the training data comprising bacteria isolate-antibiotic pairs, generating the training data comprising: obtaining ground truth data for the microorganism, extracting the metadata from the ground truth data, and cleaning the ground truth data by transforming the metadata having been extracted into discrete data according to a type of the matrix factorization algorithm, wherein the matrix factorization algorithm learns latent factors between the first factor matrix and the second factor matrix; multiplying the first factor matrix by the second factor matrix, thereby forming a reconstruction matrix, wherein an element of the reconstruction matrix linking the microorganism to the antibiotic drug has a numerical value indicating the microorganism is resistant or susceptible to the antibiotic drug; predicting antibiotic resistance of the microorganism to the antibiotic drug according to the reconstruction matrix; and selecting the antibiotic drug to treat the microorganism in a medical therapy based on the numerical value obtained from the reconstruction matrix.

2. The method of claim 1, wherein said factoring the initial matrix is performed using k number of the latent factors, wherein k is a positive whole number greater than 1.

3. The method of claim 2, wherein k is a positive whole number between 1 and 1,000,000.

4. The method of claim 2, wherein: the initial matrix has m rows and n columns, m and n being positive integers greater than 1, the first factor matrix has m rows and k columns, and the second factor matrix has k rows and n columns; and the matrix factorization algorithm comprises weighted approximate rank pairwise (WARP) loss.

5. The method of claim 2, wherein the k number of the latent factors are determined by an iterative process comprising i) choosing an initial number of latent factors k', ii) factoring the initial matrix into a first factor matrix and a second factor matrix, iii) calculating a reconstruction matrix by multiplying the first factor matrix times the second factor matrix, iv) determining a reconstruction error between the initial matrix and the reconstruction matrix, and v) repeating i)-iv) until the reconstruction error is acceptable, wherein the initial number of latent factors is equal to k.

6. The method of claim 1, wherein each entry of the first factor matrix and the second factor matrix is zero or a positive number.

7. The method of claim 1, wherein at least one column of the initial matrix is assigned a taxonomic level.

8. The method of claim 1, wherein each unique antibiotic drug of the metadata is assigned a different column of the initial matrix.

9. The method of claim 1, wherein at least one column of the initial matrix is assigned to an antibiotic drug used in an antibiogram.

10. The method of claim 1, wherein each of the microorganisms of the initial matrix is a member of the group consisting of bacteria, fungi, viruses, protozoans, and parasites.

11. The method of claim 1, wherein at least one column of the initial matrix is assigned to an isolation source of the microorganisms.

12. A computer program product, comprising a computer readable hardware storage device having a computer-readable program code stored therein, said program code configured to be executed by a processor of a computer system to implement a method comprising: providing an initial matrix comprising rows corresponding to microorganisms and columns corresponding to metadata associated with one or more of the microorganisms, the metadata including antibiogram data, wherein an element of the initial matrix linking a microorganism to an antibiotic drug has a numerical value indicating no antibiogram data exist for the microorganism with respect to the antibiotic drug; factoring the initial matrix using a matrix factorization algorithm, thereby forming a first factor matrix and a second factor matrix, wherein training data is used to train the matrix factorization algorithm, the training data comprising bacteria isolate-antibiotic pairs, generating the training data comprising: obtaining ground truth data for the microorganism, extracting the metadata from the ground truth data, and cleaning the ground truth data by transforming the metadata having been extracted into discrete data according to a type of the matrix factorization algorithm, wherein the matrix factorization algorithm learns latent factors between the first factor matrix and the second factor matrix; multiplying the first factor matrix by the second factor matrix, thereby forming a reconstruction matrix, wherein an element of the reconstruction matrix linking the microorganism to the antibiotic drug has a numerical value indicating the microorganism is resistant or susceptible to the antibiotic drug; and selecting the antibiotic drug to treat the microorganism in a medical therapy based on the numerical value.

13. The computer product of claim 12, wherein the computer program product identifies differences between entries of the reconstruction matrix and corresponding entries of the initial matrix and provides a report of the identified differences to a user.

14. A system comprising one or more computer processor circuits configured and arranged to: provide an initial matrix comprising rows corresponding to microorganisms and columns corresponding to metadata associated with one or more of the microorganisms, the metadata including antibiogram data, wherein an element of the initial matrix linking a microorganism to an antibiotic drug has a numerical value indicating no antibiogram data exist for the microorganism with respect to the antibiotic drug; factor the initial matrix using a matrix factorization algorithm, thereby forming a first factor matrix and a second factor matrix, wherein training data is used to train the matrix factorization algorithm, the training data comprising bacteria isolate-antibiotic pairs, generating the training data comprising: obtaining ground truth data for the microorganism, extracting the metadata from the ground truth data, and cleaning the ground truth data by transforming the metadata having been extracted into discrete data according to a type of the matrix factorization algorithm, wherein the matrix factorization algorithm being configured to learn latent factors between the first factor matrix and the second factor matrix; multiply the first factor matrix by the second factor matrix, thereby forming a reconstruction matrix, wherein an element of the reconstruction matrix linking the microorganism to the antibiotic drug has a numerical value indicating the microorganism is resistant or susceptible to the antibiotic drug; and selecting the antibiotic drug to treat the microorganism in a medical therapy based on the numerical value.

15. The system of claim 14, wherein the system is located at a cloud platform.

16. A method, comprising: acquiring antibiogram data that include a table in which the rows correspond to biological samples and the columns correspond to categories of metadata; transforming the table to an adjacency matrix; analyzing the adjacency matrix with a matrix factorization algorithm, thereby finding two factor matrices, and then computing a reconstructed adjacency matrix that is the product of the two factor matrices, wherein training data is used to train the matrix factorization algorithm, the training data comprising bacteria isolate-antibiotic pairs, generating the training data comprising: obtaining ground truth data for the microorganism, extracting the metadata from the ground truth data, and cleaning the ground truth data by transforming the meta data having been extracted into discrete data according to a type of matrix factorization algorithm, wherein the matrix factorization algorithm learns latent factors between the two factor matrixes; comparing the adjacency matrix to the reconstructed adjacency matrix in an entry-wise fashion, wherein the reconstructed adjacency matrix has an entry linking a microorganism to an antibiotic drug, the microorganism having no previously known resistance and/or susceptibility to the antibiotic drug, the entry having a numerical value indicating the microorganism is resistant and/or susceptible to the antibiotic drug; and selecting the antibiotic drug to treat the microorganism in a medical therapy based on the numerical value.

17. The method of claim 16, wherein the transforming includes the following steps: collecting all the entries from the table of antibiogram data and identifying unique instances of the metadata; constructing the adjacency matrix wherein the rows are biological samples and the columns are unique instances of the metadata; and setting the entries of the adjacency matrix to "1"s for the pairs of biological samples and metadata instances that occur in the antibiogram data, and setting the entries of the adjacency matrix to "0"s for the pairs of biological samples and metadata instances that do not occur in the antibiogram data.

18. The method of claim 16, wherein: if an entry value of a cell in the input adjacency matrix is 0 and an entry value of a corresponding cell in the reconstructed adjacency matrix is greater than 0, the entry value of the corresponding cell in the reconstructed adjacency matrix is interpreted as a prediction score associating a respective biosample (row index) with a metadata instance (column index).

19. The method of claim 18, wherein prediction scores of the reconstructed adjacency matrix are ranked by their values and thresholds, thereby identifying the most relevant predictions that are then output to a user of the method.

20. The method of claim 16, wherein the samples are bacterial isolates.

21. The method of claim 16, wherein the metadata include the names of antibiotics.

* * * * *